US008034370B2

(12) United States Patent
Shiah et al.

(10) Patent No.: US 8,034,370 B2
(45) Date of Patent: *Oct. 11, 2011

(54) OCULAR IMPLANT MADE BY A DOUBLE EXTRUSION PROCESS

(75) Inventors: Jane-Guo Shiah, Irvine, CA (US); Rahul Bhagat, Irvine, CA (US); Wendy M. Blanda, Tustin, CA (US); Thierry Nivaggioli, Los Altos, CA (US); Lin Peng, Palo Alto, CA (US); David Chou, Palo Alto, CA (US); David A. Weber, Danville, CA (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/931,954

(22) Filed: Oct. 31, 2007
(Under 37 CFR 1.47)

(65) Prior Publication Data
US 2008/0107712 A1    May 8, 2008

Related U.S. Application Data

(63) Continuation of application No. 10/918,597, filed on Aug. 13, 2004, which is a continuation-in-part of application No. 10/340,237, filed on Jan. 9, 2003.

(51) Int. Cl.
A61K 9/00 (2006.01)
A61K 31/56 (2006.01)
(52) U.S. Cl. .................................... 424/428; 514/180
(58) Field of Classification Search .................. None
See application file for complete search history.

(56) References Cited

U.S. PATENT DOCUMENTS

| 3,416,530 | A | 12/1968 | Ness |
| 3,432,592 | A | 3/1969 | Speiser |
| 3,845,770 | A | 11/1974 | Theeuwes et al. |
| 3,914,402 | A | 10/1975 | Shell |
| 3,916,899 | A | 11/1975 | Theeuwes et al. |
| 3,921,632 | A | 11/1975 | Bardani |
| 3,961,628 | A | 6/1976 | Arnold |
| 3,986,510 | A | 10/1976 | Higuchi et al. |
| 4,008,864 | A | 2/1977 | Torphammar et al. |
| 4,014,334 | A | 3/1977 | Theeuwes et al. |
| 4,063,064 | A | 12/1977 | Saunders et al. |
| 4,088,864 | A | 5/1978 | Theeuwes et al. |
| 4,144,317 | A | 3/1979 | Higuchi et al. |
| 4,180,646 | A | 12/1979 | Choi et al. |
| 4,186,184 | A | 1/1980 | Zaffaroni |
| 4,200,098 | A | 4/1980 | Ayer et al. |
| 4,201,210 | A | 5/1980 | Hughes et al. |
| 4,285,987 | A | 8/1981 | Ayer et al. |
| 4,300,557 | A | 11/1981 | Refojo et al. |
| 4,304,765 | A | 12/1981 | Shell et al. |
| 4,327,725 | A | 5/1982 | Cortese et al. |
| 4,402,979 | A | 9/1983 | Shen et al. |
| 4,451,254 | A | 5/1984 | Dinius et al. |
| 4,474,451 | A | 10/1984 | Mizokami |
| 4,478,818 | A | 10/1984 | Shell et al. |
| 4,494,274 | A | 1/1985 | Thurlow |
| 4,521,210 | A | 6/1985 | Wong |
| 4,599,353 | A | 7/1986 | Bito |
| 4,668,506 | A | 5/1987 | Bawa |
| 4,756,911 | A | 7/1988 | Drost et al. |
| 4,801,460 | A | 1/1989 | Goertz et al. |
| 4,806,337 | A | 2/1989 | Snipes et al. |
| 4,853,224 | A | 8/1989 | Wong |
| 4,863,457 | A | 9/1989 | Lee |
| 4,865,846 | A | 9/1989 | Kaufman |
| 4,945,089 | A | 7/1990 | Clark |
| 4,959,217 | A | 9/1990 | Sanders et al. |
| 4,966,849 | A | 10/1990 | Vallee et al. |
| 4,997,652 | A | 3/1991 | Wong |
| 5,004,601 | A | 4/1991 | Snipes |
| 5,004,614 | A | 4/1991 | Staniforth |
| 5,006,342 | A | 4/1991 | Cleary et al. |
| 5,019,400 | A | 5/1991 | Gombotz |
| 5,028,624 | A | 7/1991 | Chan et al. |
| 5,034,413 | A | 7/1991 | Chan et al. |
| 5,075,115 | A | 12/1991 | Brine |
| 5,082,655 | A | 1/1992 | Snipes et al. |
| 5,164,188 | A | 11/1992 | Wong |
| 5,169,638 | A | 12/1992 | Dennis et al. |
| 5,268,178 | A | 12/1993 | Calhoun et al. |
| 5,314,419 | A | 5/1994 | Pelling |
| 5,322,691 | A | 6/1994 | Darougar et al. |
| 5,330,992 | A | 7/1994 | Eissenstat et al. |

(Continued)

FOREIGN PATENT DOCUMENTS
CA    1333770    10/1988
(Continued)

OTHER PUBLICATIONS

Zhou et al. (Journal of Controlled Release. 1998; 55: 281-295).*
U.S. Appl. No. 07/357,394, filed May 1989.
U.S. Appl. No. 07/386,835, filed Jul. 1989.
U.S. Appl. No. 10/820,563, filed Apr. 2004.
U.S. Appl. No. 60/587,092, filed Jul. 2004.
Aguilar, H.E., et al. "Vancomycin Levels After Intravitreal Injection," *Retina*, 1995; 15:428-432.
Ahmad, M., et al. "Ortho Ester Hydrolysis: Direct Evidence for a Three-Stage Reaction Mechanism," *Journal of American Chemistry*, 1979; 101(10):2669-2677.
Ahmed, I., et al. "Macular disorders: cystoid macular edema," *Ophthalmology*, Yanoff, M., Duker, J.S., eds. London: Mosby, 1999; 34.1-34.6.
Akduman, L., et al. "The early treatment diabetic retinopathy study," *Clinical trials in ophthalmology: a summary and practice guide*, Kertes, P.S., Conway, M.D., eds. Baltimore: Williams & Wilkins, 1998; 15-35.

(Continued)

Primary Examiner — Shanon A Foley
(74) *Attorney, Agent, or Firm* — Louis V. Wollenberge; Joel B. German; Debra D. Condino

(57) ABSTRACT

The invention provides biodegradable implants sized for implantation in an ocular region and methods for treating medical conditions of the eye. The implants are formed from a mixture of hydrophilic end and hydrophobic end PLGA, and deliver active agents into an ocular region without a high burst release.

8 Claims, 17 Drawing Sheets

U.S. PATENT DOCUMENTS

| | | | |
|---|---|---|---|
| 5,356,629 A | 10/1994 | Sander et al. | |
| 5,378,475 A | 1/1995 | Smith et al. | |
| 5,384,333 A | 1/1995 | Davis et al. | |
| 5,385,887 A | 1/1995 | Yim et al. | |
| 5,443,505 A | 8/1995 | Wong et al. | |
| 5,476,511 A | 12/1995 | Gwon et al. | |
| 5,501,856 A | 3/1996 | Ohtori et al. | |
| 5,597,897 A | 1/1997 | Ron et al. | |
| 5,601,844 A | 2/1997 | Kagayama et al. | |
| 5,656,297 A | 8/1997 | Bernstein et al. | |
| 5,660,847 A | 8/1997 | Magruder et al. | |
| 5,660,851 A | 8/1997 | Domb | |
| 5,688,819 A | 11/1997 | Woodward et al. | |
| 5,693,335 A | 12/1997 | Xia et al. | |
| 5,707,643 A | 1/1998 | Ogura | |
| 5,755,785 A | 5/1998 | Rowsey et al. | |
| 5,766,242 A | 6/1998 | Wong et al. | |
| 5,773,019 A | 6/1998 | Ashton et al. | |
| 5,773,021 A | 6/1998 | Gurtler et al. | |
| 5,824,072 A | 10/1998 | Wong | |
| 5,824,074 A | 10/1998 | Koch | |
| 5,869,079 A * | 2/1999 | Wong et al. | 424/426 |
| 5,882,682 A | 3/1999 | Rork et al. | |
| 5,902,598 A | 5/1999 | Chen et al. | |
| 5,941,250 A | 8/1999 | Aramant et al. | |
| 5,962,027 A | 10/1999 | Hughes | |
| 5,972,369 A | 10/1999 | Roorda et al. | |
| 6,045,791 A | 4/2000 | Liu | |
| 6,046,187 A | 4/2000 | Berde et al. | |
| 6,051,576 A | 4/2000 | Ashton et al. | |
| 6,063,116 A | 5/2000 | Kelleher | |
| 6,074,661 A | 6/2000 | Olejnik et al. | |
| 6,217,895 B1 | 4/2001 | Guo et al. | |
| 6,217,911 B1 | 4/2001 | Vaugn et al. | |
| 6,309,669 B1 | 10/2001 | Setterstrom et al. | |
| 6,329,369 B1 | 12/2001 | Chow et al. | |
| 6,331,313 B1 | 12/2001 | Wong et al. | |
| 6,369,116 B1 | 4/2002 | Wong et al. | |
| 6,403,649 B1 | 6/2002 | Woodward et al. | |
| 6,497,729 B1 | 12/2002 | Moussy et al. | |
| 6,534,542 B2 | 3/2003 | Chow et al. | |
| 6,537,568 B2 | 3/2003 | Olejnik et al. | |
| 6,545,182 B2 | 4/2003 | Chow et al. | |
| 6,548,078 B2 | 4/2003 | Guo et al. | |
| 6,586,006 B2 * | 7/2003 | Roser et al. | 424/484 |
| 6,699,493 B2 * | 3/2004 | Wong | 424/428 |
| 6,713,081 B2 | 3/2004 | Robinson et al. | |
| 6,726,918 B1 | 4/2004 | Wong et al. | |
| 6,841,684 B2 | 1/2005 | Chow et al. | |
| 7,048,946 B1 | 5/2006 | Wong et al. | |
| 7,091,232 B2 | 8/2006 | Chow et al. | |
| 7,141,597 B2 | 11/2006 | Chow et al. | |
| 7,276,522 B2 | 10/2007 | Heidelbaugh et al. | |
| 7,335,803 B2 | 2/2008 | Chow et al. | |
| 2004/0019098 A1 | 1/2004 | Andrews et al. | |
| 2004/0132824 A1 | 7/2004 | Gil et al. | |
| 2004/0137059 A1 | 7/2004 | Nivagioli et al. | |
| 2004/0151753 A1 | 8/2004 | Chen | |
| 2004/0170665 A1 | 9/2004 | Donovan | |
| 2004/0266776 A1 | 12/2004 | Gil et al. | |
| 2005/0048099 A1 | 3/2005 | Shiah et al. | |
| 2005/0058696 A1 | 3/2005 | Donello et al. | |
| 2005/0059664 A1 | 3/2005 | Gil et al. | |
| 2005/0059744 A1 | 3/2005 | Donello et al. | |
| 2005/0101582 A1 | 5/2005 | Lyons et al. | |
| 2005/0181017 A1 | 8/2005 | Hughes et al. | |
| 2005/0232966 A1 | 10/2005 | Hughes et al. | |
| 2005/0244464 A1 | 11/2005 | Hughes et al. | |
| 2005/0244469 A1 | 11/2005 | Whitcup et al. | |
| 2005/0244474 A1 | 11/2005 | Huang et al. | |
| 2006/0009498 A1 | 1/2006 | Whitcup | |
| 2006/0233859 A1 | 10/2006 | Whitcup et al. | |
| 2007/0224246 A1 | 9/2007 | Hughes et al. | |
| 2007/0298073 A1 | 12/2007 | Whitcup et al. | |

FOREIGN PATENT DOCUMENTS

| | | |
|---|---|---|
| CA | 2336703 | 1/2000 |
| EP | 0 052 916 | 7/1981 |
| EP | 0 102 265 | 3/1984 |
| EP | 0 197 718 | 3/1986 |
| EP | 0 322 319 | 6/1989 |
| EP | 0 364 417 | 9/1989 |
| EP | 0 430 539 | 6/1991 |
| EP | 0 474 098 | 3/1992 |
| EP | 0 488 401 | 6/1992 |
| EP | 0 654 256 | 5/1995 |
| EP | 0 311 065 | 10/1998 |
| EP | 0 992 244 | 4/2000 |
| WO | WO 91/15495 | 10/1991 |
| WO | WO 91/18940 | 12/1991 |
| WO | WO 92/21660 | 12/1992 |
| WO | WO 93/10141 | 5/1993 |
| WO | WO 94/03427 | 2/1994 |
| WO | WO 94/10202 | 5/1994 |
| WO | WO 94/14808 | 7/1994 |
| WO | WO 94/18956 | 9/1994 |
| WO | WO 95/13765 | 5/1995 |
| WO | WO 96/38174 | 12/1996 |
| WO | WO 97/26869 | 7/1997 |
| WO | WO 98/22130 | 5/1998 |
| WO | WO 99/11244 | 3/1999 |
| WO | WO 00/02564 | 1/2000 |
| WO | WO 00/37056 | 6/2000 |
| WO | WO 00/56340 | 9/2000 |
| WO | WO 00/62760 | 10/2000 |
| WO | WO 01/30323 | 5/2001 |
| WO | WO 02/02076 | 1/2002 |
| WO | WO 02/43785 | 6/2002 |
| WO | WO 03/094888 | 5/2003 |
| WO | WO 2004/026106 | 4/2004 |
| WO | WO 2004/062649 | 7/2004 |
| WO | WO 2005/110362 | 4/2005 |
| WO | WO 2006/093758 | 9/2006 |
| WO | WO 2007/130945 | 11/2007 |

OTHER PUBLICATIONS

Algvere, P.V., et al. "Transplantation of RPE in Age-Related Macular Degeneration: Observations in Disciform Lesions and Dry RPE Atrophy," *Graefe's Archives of Clinical Experimental Ophthalmology*, 1997; 235(3):149-158.

Anderson, L.C., et al. "An Injectable Substained Release Fertility Control System," *Contraception*, 1976; 13:375-384.

Andreau, K., et al. "Induction of apoptosis by dexamethasone in the B cell lineage," *Immunopharmacology*, Jul. 1998; 40(1):67-76.

Antcliff, R., et al. "The pathogenesis of edema in diabetic maculopathy," *Seminars in Ophthalmology*, 1999; 14:223-232.

Apel, A., et al. "A Subconjunctival Degradable Implant for Cyclosporine Delivery in Corneal Transplant Therapy," *Current Eye Research*, 1995; 14(8):659-667.

Araie, M. and Maurice, D.M. "The Loss of Fluorescein, Fluorescein Glucuronide and Fluorescein Isothiocyanate Dextran From the Vitreous by the anterior and Retinal Pathways," *Experimental Eye Research*, 1991; 52:27-39.

Baker, R. "Monolithic Devices," *Controlled Release of Biologically Active Agents*, New York: John Wiley & Sons, 1987; 50-75.

Barnas, U., et al. "Parameters Associated with Chronic Renal Transplant Failure," *Nephrology Dialysis Transplantation*, 1997; 12(Suppl 2):82-85.

Barza, M., et al. "Pharmacokinetics of Intravitreal Carbenicillin, Cefazolin, and Gentamicin in Rhesus Monkeys," *Investigative Ophthalmology & Visual Science*, 1983; 24:1602-1606.

Beck, R.W. "The Effect of Corticosteroids for Acute Optic Neuritis on the Subsequent Development of Multiple Sclerosis," *New England Journal of Medicine*, 1993; 329(24):1764-1769.

Beck, R.W., et al. "A randomized, controlled trial of corticosteroids in the treatment of acute optic neuritis," *New England Journal of Medicine*, Feb. 27, 1992; 326(9):634-5.

Bennett, W.M. and Barry, J.M. "Failure of Dexamethasone to Provide Adequate Chronic Immunosuppression for Renal Transplantation," *Transplantation*, 1979; 27(3):218-219.

Ben-Nun, J., et al. "Pharmacokinetics of Intravitreal Injection," *Investigative Ophthalmology & Visual Science* 1989; 30(6):1055-1061.

Bigar, F. and C.P. Herbort. "Corneal Transplantation," *Current Opinion in Ophthalmology*, 1992; 3(4):473-481.

Bingaman, D.P., et al. "Inhibition of preretinal neovascularization in pigs by intravitreal triamcinolone acetonide," *Investigative Ophthalmology and Visual Science*, 1995; 36(4):S401, abstract 1867.

Bito, L.Z. "Prostaglandins and Related Compounds as Potential Ocular Therapeutic Agents," *Biological Protection with Prostaglandins*, vol. 1, Cohen, M.M. ed., Boca Raton: CRC Press Inc., 1985; 31-252.

Bito, L.Z. "Prostaglandins, Other Eicosanoids, and their Derivatives as Potential Antiglaucoma Agents," *Glaucoma: Applied Pharmacology in Medical Treatment*, Drance, S.M. and Neufled, A.H. Eds., New York: Grune & Stratton, 1984; 477-505.

Bito, L.Z. "Prostaglandins: Old Concepts and New Perspectives," *Archives of Ophthalmology*, 1987; 105:1036-1039.

Bloch-Michel, E. "Opening Address: Intermediate Uveitis," *Developments in Ophthalmology: Intermediate Uveitis*, W.R.F. Böke, et al. eds. Basel: Karger, 1992; 23:1-2.

Bodor, N., et al. "A Comparison of Intraocular Pressure Elevating Activity of Loteprednol Etabonate and Dexamethasone in Rabbits," *Current Eye Research*, 1992; 11(6):525-530.

Böke, W.R.F. "Clinical Picture of Intermediate Uveitis," *Developments in Ophthalmology: Intermediate Uveitis*, W.R.F. Böake, et al. eds. Basel: Karger 1992; (23):20-27.

Bolen, J.B. "Nonreceptor tyrosine protein kinases," *Oncogene*, 1993; 8(8):2025-2031.

Brubaker, R.F. "Mechanism of Action of Bimatoprost (Lumigan™)," *Survey of Ophthalmology*, 2001; 45(Suppl 4):S347-S351.

Budavari, S., et al. eds. *The Merck Index*, $12^{th}$ ed. Rahway, NJ: Merck and Co., 1996; Table of Contents only.

Bundgaard, H. and Møss, J. "Prodrugs of Peptides IV: Bioreversible Derivatization of the Pyroglutamyl Group by N-Acylation and N-Aminomethylation to Effect Protection against Pyroglutamyl Aminopeptidease," *Journal of Pharmaceutical Sciences*, 1989; 78(2):122-126.

Burdon, M.A. and P. McDonnell. "A Survey of Corneal Graft Practice in the United Kingdom," *Eye*, 1995; 9(Suppl):6-12.

Chacko, D.M., et al. "Survival and Differentiation of Cultured Retinal Progenitors Transplanted in the Subretinal Space of the Rat," *Biochemical and Biophysical Research Communications*, 2000; 268(3):842-846.

Challa, J.K., et al. "Exudative Macular Degeneration and Intravitreal Triamcinolone: 18 month follow up," *Australian and New Zealand Journal of Ophthalmology*, 1998; 26:277-281.

Chang, David, et al. "Phase II results of an intraocular steroid delivery system for cataract surgery," *Ophthalmology*, Jun. 1996; 106(6):1172-1177.

Chang, M., et al. "Basic Science and Clinical Aspects of Wound Healing in Glaucoma Filtering Surgery," *Journal of Ocular Pharmacology and Therapeutics*, 1998; 14(1):75-95.

Charles, J., et al. "Use of Bioerodible Polymers Impregnated with Mitomycin in Glaucoma Filtration Surgery in Rabbits," *Ophthalmology*, Apr. 1991; 98(4):503-508.

Chen, J., et al. "Lumigan®: A Novel Drug for Glaucoma Therapy," *Optometry in Practice*, 2002; 3:95-102.

Cheng, Cheng-Kuo, et al. "Intravitreal Sustained-Release Dexamethasone Device in the Treatment of Experimental Uveitis," *Investigative Ophthalmology & Visual Science*, Feb. 1995; 36(2):442-453.

Clarkson, J.G. "Central retinal vein occlusion," *Retina*, $3^{rd}$ ed. Ryan, S., Schachat, A.P.,eds. St. Louis, MO: CV Mosby; 2001; 1368-1375.

Coleman, A.L., et al. "A 3-Month Randomized Controlled Trial of Bimatoprost (LUMIGAN) Versus Combined Timolol and Dorzolamide (Cosopt) in Patients with Glaucoma or Ocular Hypertension," *Ophthalmology*, 2003; 110(12):2362-2368.

Cuff, G. and Raouf, F. "A Preliminary Evaluation of Injection Molding as a Technology to Produce Tablets," *Pharmaceutical Technology*, 1998; 96-106.

Davis, P.A., et al. "Intraocular Implant for Controlled 5-Fluorouracil Release," *Proceedings of the 19th International Symposium of Controlled Release Bioactive Materials*, 1992; 19:339-340.

De Jong, S.J., et al. "New insights into the hydrolytic degradation of poly(lactic acid): participation of the alcohol terminus," *Polymer*, 2001; 42:2795-2802.

Di Colo, G. "Controlled Drug Release From Implantable Matrices Based on Hydrophobic Polymers," *Biomaterials*, 1992; 13(12):850-856.

Dick, J., et al. "Macular edema," *Retina*, $3^{rd}$ ed. Ryan, S., Schachat, A.P., eds. St. Louis, MO: CV Mosby; 2001; 967-979.

Dinning, W.J. "Intermediate Uveitis: history, terminology definition pars planitis: systemic disease associations," *Developments in Ophthalmology: Intermediate Uveitis*, W.R.F. Böke, et al. eds. Basel: Karger, 1992; 3-8.

Dohlman, C., et al. "Treatment of corneal edema with a buried implant," *Transactions: American Academy of Ophthalmology and Otolaryngology*, Mar.-Apr. 1966; 267-280.

Druilhe, A., et al. "Glucocorticoid-induced apoptosis in human eosinophils: mechanisms of action," *Apoptosis*, Oct. 2003; 8(5):481-95.

*Encyclopedia of Polymer Science and Technology*, vol. 3. New York: Interscience Publishers, Inc., 2003; Table of Contents only, v.

Enyedi, Laura, et al. "An Intravitreal Device Providing Sustained Release of Cyclosporine and Dexamethasone," *Current Eye Research*, 1996; 15(5):549-557.

Enzmann, V., et al. "Immunological Problems of Transplantation into the Subretinal Space," *Acta Anatomica*, 1998; 162(2-3):178-183.

Fatt, I. "Flow and Diffusion in the Vitreous Body of the Eye," *Bulletin of Mathematical Biology*, 1975; 37:85-90.

Fekrat, S. and Finkelstein, D. "The Central Vein Occlusion Study," *Clinical trials in ophthalmology: a summary and practice guide*, Kertes, P.S., Conway, M.D., eds. Baltimore, MD: Williams & Wilkins, 1998; 129-143.

Frank, R.N. "Etiologic mechanisms in diabetic retinopathy," *Retina*, $3^{rd}$ ed. Ryan, S., Schachat,, A.P., eds. St. Louis, MO: CV Mosby; 2001; 1259-1294.

Friedrich, S., et al. "Finite Element Modeling of Drug Distribution in the Vitreous Humor of the Rabbit Eye," *Annals of Biomedical Engineering*, 1997; 25:303-314.

Gennaro, A.R. ed. *Remington: The Science and Practice of Pharmacy*, $19^{th}$ Ed. Easton, PA: Mack Publishing Company, 1995; Table of Contents only, xv-xvi.

Gillies, M.C., et al. "Safety of an intravitreal injection of triamcinolone," *Archives of Ophthalmology*, Mar. 2004; 122:336-340.

Gilman, A.G., et al. eds. *Goodman and Gilman's: The Pharmacological Basis of Therapeutics*. $8^{th}$ Ed. New York: Pergamon Press, 1990; Table of Contents only, xi-xvi.

Goldberg, Ivan, "Drugs for glaucoma," *Australian Prescriber*, 2002; 25(6)142-146.

Goodman, L.S. and A. Gilman eds. *The Pharmacological Basis of Therapeutics*, $9^{th}$ Ed. New York: McGraw-Hill, 1996; Table of Contents only, v-xii.

Gould, L., et al. "Fifty:fifty Poly (DL Glycolic Acid-Lactic Acid) Copolymer as a Drug Delivery System for 5-Fluorouracil: A Histopathological Evaluation," *Canadian Journal of Ophthalmology*, 1994; 29(4):168-171.

Greenfield, R.S., et al. "Evaluation in Vitro of Adriamycin Immunoconjugates Synthesized Using an Acid-sensitive Hydrazone Linker," *Cancer Research*, 1990; 50:6600-6607.

Guan, D., et al. "The Therapeutic Window of Cyclosporine in Chinese Recipients of Renal Transplantation," *Transplantation Proceedings*, 1995; 27(1):850-851.

Hainsworth, Dean P., et al. "Sustained Release Intravitreal Dexamethasone," *Journal of Ocular Pharmacology and Therapeutics*, 1996; 12(1):57-63.

Hari, P. and Srivastava, R.N. "Pulse Corticosteroid Therapy with Methylprednisolone or Dexamethasone," *Indian Journal of Pediatrics*, 1998; 65(3):557-560.

Haynes, Robert C. Jr. "Adrenocorticotropic Hormone; Adrenocortical Steroids and their Synthetic Analogs; Inhibitors of the Synthesis and Actions of Adrenocortical Hormones," *Goodman and Gilman's: The pharmacological Basis of Therapeutics*, 8th Ed. New York: Pergamon Press, 1990; 1431-1462.

Hayreh, S.S. "Posterior Drainage of the Intraocular Fluid From the Vitreous," *Experimental Eye Research*, 1996; 5:123-144.

Heller, J. "Biodegradable Polymers in Controlled Drug Delivery," *CRC Critical Reviews in Therapeutic Drug Carrier Systems*, 1984; 1(1):39-90.

Heller, J. "Bioerodible Hydrogels," *Hydrogels in Medicine and Pharmacy, vol. 3: Properties and Applications*, Peppas, N.A. ed. Boca Raton: CRC Press, 1987; 138-149.

Heller, J. "Poly (Ortho Esters)," *Biopolymers I*, Peppas, N.A. and R.S. Langer eds. New York: Springer-Verlag, 1993; 41-92.

Heller, J., et al. "Poly(ortho ester) Biodegradable Polymer Systems," *Methods in Enzymology*, Widder, K.J. and R. Green eds. Orlando: Academic Press, Inc., 1985; 422-436.

Hirano, T. "Clinical Significance of Glucocorticoid Pharmacodynamics Assessed by Antilymphocyte Action in Kidney Transplantation," *Transplantation*, 1994; 57(9):1341-1348.

Höckel, M., et al. "Prevention of Peritoneal Adhesions in the Rat With Sustained Intraperitoneal Dexamethasone Delivered by a Novel Therapeutic System," *Annales Chirurgiae et Gynaecologiae*, 1987; 76(6):306-313.

Inoue, M., et al. "Vitreous Concentrations of Triamcinolone Acetonide in Human Eyes After Intravitreal or Subtenon Injection," *American Journal of Ophthalmology*, 2004; 138(6):1046-8.

Jackanicz, T., et al. "Polyactic Acid As a Biogradable Carrier for Contraceptive Steroids" *Contraception*, 1973; 8(3):227-234.

Jaffe, G.J., et al. "Safety and Pharmacokinetics of an Intraocular Fluocinolone Acetonide Sustained Delivery Device," *Investigative Ophthalmology & Visual Science*, 2000; 41(11):3569-3575.

Jaffe, G.J., et al. "Safety, Efficacy, and Pharmacokinetics of an Intravitreal Fluocinolone Sustained Drug Delivered System," *Investigative Ophthalmology & Visual Science*, 1999; 40(4):S988, abstract 5195.

Jampel, H., et al. "Glaucoma Filtration Surgery in Monkeys Using 5-Fluorouridine in Polyanhydride Disks," *Archives of Ophthalmology*, Mar. 1990; 108(3):430-435.

Jay, W.M., et al. "Intravitreal Ceftazidime in a Rabbit Model: Dose- and Time-Dependent Toxicity and Pharmacokinetic Analysis," *Journal of Ocular Pharmacology*, 1987; 3(3):257-262.

Jellinek, D., et al. "Inhibition of Receptor binding by High-affinity RNA Ligands to Vascular Endothelial Growth Factor," *Biochemistry*, 1994; 33:10450-56.

Jennings, T., et al. "Posterior sub-Tenon's injections of corticosteroids in uveitis patients with cystoid macular edema," *Japanese Journal of Ophthalmology*, 1988; 32(4):385-391.

Jeong, J.H., et al. "Novel Intracellular Delivery System of Antisense Oligonucleotide by Self-Assembled Hybrid Micelles Composed of DNA/PEG Conjugate and Cationic Fusogenic Peptide," *Bioconjugate Chemistry*, 2003; 14:473-479.

Johnson, F. and Maurice, D. "A Simple Method of Measuring Aqueous Humor Flow With Intravitreal Fluoresceinated Dextrans," *Experimental Eye Research*, 1984; 39:791-805.

Jonas, J.B., et al. "Intraocular pressure after intravitreal injection of triamcinolone acetonide," *British Journal of Ophthalmology*, 2003; 87:24-27.

Kane, A., et al. "Intravitreal Injection of Gentamicin in Rabbits," *Investigative Ophthalmology & Visual Science*, 1981; 20(5):593-597.

Kang, S.W., et al. "Macular grid photocoagulation after intravitreal triamcinolone acetonide for diffuse diabetic macular edema," *Archives of Ophthalmology*, May 2006; 124(5):653-8.

Kendall, R.L and K.A. Thomas. "Inhibition of vascular endothelial cell growth factor activity by an endogenously encoded soluble receptor," *Proceedings of the National Academy of Science USA*, 1994; 90:10705-09.

Kher, V., et al. "Low-Dose Dexamethasone—An Alternative Therapy for Acute Renal Allograft Rejection," *Transplantation Proceedings*, 1992; 24(5):1725.

Kim, K.J., et al. "Inhibition of vascular endothelial growth factor-induced angiogenesis suppresses tumour growth in vivo," *Nature*, 1993; 362(6423):841-844.

Kimura, H. and Ogura, Y. "Biodegradable Polymers for Ocular Drug Delivery," *Ophthalmologica*, 2001; 215:143-155.

Kinsella, J.L., et al. "Protein Kinase C Regulates Endothelial Cell Tube Formation on Basement Membrane Matrix, Matrigel," *Experimental Cell Research*, 1992; 199:56-62.

Kochinke, F. and Wong, V.G. "Biogradable Drug Delivery System for Uveitis Treatment, Oculex Pharmaceuticals, Inc.," Slide Presentation, 1996; total pages 20.

Kochinke, F., et al. "Biodegradable Drug Delivery System for Uveitis Treatment," *Investigative Ophthalmology & Visual Science*, Feb. 1996; 37(3):S42.

Kralinger, M.T., et al. "Slow Release of Acetysalicyclic Acid by Intravitreal Silicone Oil," *Retina: The Journal of Retinal and Vitreous Diseases*, 2001; 21(5):513-520.

Kunou, Noriyuki, et al. "Biodegradable scleral implant for controlled intraocular delivery of betamethasone phosphate," *Journal of Biomedical Materials Research*, 2000; 51(4):635-641.

Kwak, H.W. and D'Amico, D.J. "Evaluation of the Retinal Toxicity and Pharmacokinetics of Dexamethasone After Intravitreal Injection," *Archives of Ophthalmology*, 1992; 110:259-266.

Laurent, U.B.G. and Fraser, J.R.E. "Turnover of Hyaluronate in the Aqueous Humor and Vitreous Body of the Rabbit," *Experimental Eye Research*, 1983; 36:493-504.

Lee, D., et al. "Complications of Subconjunctival 5-Fluorouracil Following Glaucoma Filtering Surgery," *Ophthalmic Surgery*, Mar. 1987; 18(3):187-190.

Lee, D., et al. "Glaucoma Filtration Surgery in Rabbits Using Bioerodible Polymers and 5-Fluorouracil," *Ophthalmology*, Dec. 1987; 94(12):1523-1530.

Lee, D., et al. "The Use of Bioerodible Polymers and 5-Fluorouracil in Glaucoma Filtration Surgery," *Investigative Ophthalmology & Visual Science*, Nov. 1988; 29(11):1692-1697.

Lee, K.Y. and Wong, V.G. "Dexamethasone Posterior Segment Drug Delivery System for Treatment of Severe Uveitis," *American Uveitis Society*, 1999; Abstract.

Lee, V.H.L., et al. "Drug Delivery to the Posterior Segment" *Retina*, $3^{rd}$ ed. T.E. Ogden and A.P. Schachat eds. St. Louis: CV Mosby, 1989; 483-498.

Leopold, I.H. "Nonsteroidal and steroidal anti-inflammatory agents," *Surgical pharmacology of the Eye*, Sears, M., Tarkkanen, A., eds. New York: Raven Press, 1985; 83-133.

Marcon, I. "A double-masked comparison of betaxolol and levobunolol for the treatment of primary open-angle glaucoma," *Arquivos Brasileiros de Oftalmologia*, 1990; 53(1):27-32.

Mariani, M., et al. "Inhibition of angiogenesis by FCE 26806, a potent tyrosine kinase inhibitor," *Proceedings of the American Association for Cancer Research*, 1994; 35:381, abstract 2268.

Mathebula, S.D. "A Review of Pharmacological Therapy for Glaucoma," *The South African Optometrist*, Sep. 2005; 64(3):89-96.

Maurice, D.M. "The Exchange of Sodium Between the Vitreous Body and the Blood and Aqueous Humour," *Journal of Physiology*, 1957; 137:110-125.

Maurice, D.M. "Flow of Water Between Aqueous and Vitreous Compartments in the Rabbit Eye," *American Journal of Physiology*, 1987; 252 (1):F104-F108.

Maurice, D.M. "Micropharmaceutics of the Eye," *Ocular Inflammation and Therapeutics*, 1983; 1:97-102.

Maurice, D.M. and Mishima, S. "Ocular Pharmacokinetics," *Pharmacology of the Eye*, M.L. Sears ed. New York: Springer-Verlag, 1984; 19-116.

Meadows, D.L., et al. "Ocular Drug Delivery with Subconjunctival Implants," *Proceedings of the International Symposium on Controlled Release of Bioactive Materials*, Controlled Release Society, Inc., 1994; 21:593-594.

Migita, K., et al. "Apoptosis Induction in Human Peripheral Blood T Lymphocytes by High-Dose Steroid Therapy", *Transplantation*, 1997; 63(4):583-587.

Miller, R., et al. "Degradation Rates of Oral Resorbable Implants (Polylactates and Polyglycolates): Rate Modification with Changes in PLA/PGA Copolymer Ratios," *Journal of Biomedical Materials Research*, 1977; 11(5):711-719.

Mittal, R., et al. "Treatment of Acute Rejection in Live Related Renal Allograft Recipients: A Comparison of Three Different Protocols," *Nephron*, 1977; 77(2):186-189.

Molfino, F., et al. "IOP-lowering effect of dorzolamide 2% versus brimonidine tartrate 0.2%. A prospective randomized cross over study," *Investigative Ophthalmology & Visual Science*, Mar. 1998; 39(4):S481.

Morita Y., et al. "Intravitreous delivery of dexamethasone sodium *m*-sulfobenzoate from poly (DL-lactic acid) implants," *Biological & Pharmaceutical Bulletin*, Feb. 1998; 21(2):188-90.

Morita, Y., et al. "Polymer Blend Implant for Ocular Delivery of Fluoromethorone," *Biological & Pharmaceutical Bulletin*, 1998; 21(1):72-75.

Moseley, H., et al. "Routes of Clearance of Radioactive Water From the Rabbit Vitreous," *British Journal of Ophthalmology*, 1984; 68:145-151.

Nakamura, O., et al. "Inhibition of neovascularization and tumor growth by dexamethasone," *No to Shinkei (Brain and Nerve)*, Jan. 1992; 44(1):37-41.

Nauck, M., et al. "Corticosteroids inhibit the expression of the vascular endothelial growth factor gene in human vascular smooth muscle cells," *European Journal of Pharmacology*, 1998; 341:309-315.

Nauck, M., et al. "Induction of vascular endothelial growth factor by platelet-activating factor and platelet-derived growth factor is downregulated by corticosteroids," *American Journal of Respiratory Cell and Molecular Biology*, 1997; 16:398-406.

Nilsson, S.F.E., et al. "PGF2 Increases Uveoscleral Outflow," *Investigative Ophthalmology & Visual Science*, 1987; 28(3):284, abstract 9.

Ogden, T.E., et al. eds. *Retina—Basic Science and Inherited Retinal Disease* vol. 1, St. Louis: CV Mosby, 1994; Table of Contents, xxiii-xxix.

Ohtori, A. and Tojo, K. "In vivo/in vitro Correlation of Intravitreal Delivery of Drugs With the Help of Computer Simulation," *Biological & Pharmaceutical Bulletin*, 1994; 17(2):283-290.

Olsen, T.W., et al. "Human Scleral Permeability: Effects of Age, Cryotherapy, Transscleral Diode Laser, and Surgical Thinning," *Investigative Ophthalmology & Visual Science*, 1995; 36(9):1893-1903.

Oplinger, N.L., et al. "A Comparison of Corneal Autografts With Homografts," *Ophthalmic Surgery and Lasers*, 1998; 29(4):305-308.

Orth, D. "The branch vein occlusion study," *Clinical trials in ophthalmology: A summary and practice guide*, Kertes, P, and Conway, M, eds., Baltimore, MD: Williams & Wilkins, 1998: 113-127.

Park, T.G., et al. "A new preparation method for protein loaded poly (D,L-lactic-co-glycolic acid) microspheres and protein release mechanism study," *Journal of Controlled Release*, 1998; 55: 181-191.

Patel, N P., et al. "Indications for and Outcomes of Repeat Penetrating Keratoplasty, 1989-1995," *Ophthalmology*, 2000; 107(4):719-724.

Pearson, P.A., et al. "Clearance and Distribution of Ciprofloxacin After Intravitreal Injection," *Retina*, 1993; 13:326-330.

Pe'er, J., et al. "Vascular endothelial growth factor by platelet-activating factor upregulation in human central retinal vein occlusion," *Ophthalmology*, 1998; 105:412-416.

Peyman, G.A. and Herbst, R. "Bacterial endophthalmitis," *Archives of Ophthalmology*, 1974; 91(5):416-418.

Peyman, G.A., et al. "A Technique for Retinal Pigment Epithelium Transplantation for Age-Related Macular Degeneration Secondary to Extensive Subfoveal Scarring," *Ophthalmic Surgery*, 1991; 22(2):102-108.

Pinar, V. "Intermediate Uveitis," *Massachusetts Eye & Ear Infirmary Immunology Service*, Boston, 1998.

Plowman, G.D., et al. "Receptor Tyrosine Kinases as Targets for Drug Intervention," *Drug News & Perspectives*, 1994; 7(6): 334-339.

Rahil, J., et al. "Reactivity and Mechanism of Hydrolysis of Phosphonamides," *Journal of the American Chemical Society*, 1981; 103:1723-1734.

Rao, K.V., et al. "Successful Renal Transplantation in a Patient With Anaphylactic Reaction to Solu-Medrol (Methylprednisolone Sodium Succinate)," *American Journal of Medicine*, 1982; 72(1):161-163.

Rao, N.A., et al. "Intraocular Inflammation and Uveitis," *Basic and Clinical Science Course*, Section 9, San Francisco: American Academy of Ophthalmology, 1998-1999; 57-80, 102-103, 152-156.

Renfro, L. and Snow, J.S. "Ocular Effects of Topical and Systemic Steroids," *Dermatologic Clinics*, 1992; 10:505-512.

Riordan-Eva, P., et al. "Orbital floor steroid injections in the treatment of uveitis," *Eye*, 1994; 8(1):66-69.

Robin, Jeffrey B., et al. "The Histopathology of Corneal Neovascularization," *Archives of Ophthalmology*, 1985; 103(2):284-287.

Roff, W.J. and Scott, J.R. eds. *Handbook of Common Polymers*, Cleveland: CRC Press, 1971; Table of Contents.

Rootman, D.S., et al. "Toxicity and Pharmacokinetics of Intravitreally Injection Ciprofloxacin in Rabbit Eyes," *Canadian Journal of Ophthalmology*, 1992; 27(6):277-282.

Sasaki, H., et al. "Drug Absorption Behavior After Periocular Injections," *Biological & Pharmaceutical Bulletin*, 1999; 22(9):956-960.

Schimmer B.P. and Parker K.L. "Adrenocorticotropic hormone; Adrenocortical Steroids and their Synthetic Analogs; Inhibitors of the Synthesis and Actions of Adrenocortical Hormones," *The Pharmacological Basis of Therapeutics* $10^{th}$ ed., Hardman, J.G. and Limbard, L.L. eds, New York: McGraw-Hill, 2001; 1649-1677.

Schindler, R.H., et al. "The Clearance of Intravitreal Triamcinolone Acetonide," *American Journal of Ophthalmology*, 1982; 93(4):415-417.

Scholes, G.N., et al. "Clearance of Triamcinolone From Vitreous," *Archives of Ophthalmology*, 1985; 103(10):1567-1569.

Schwartz, B. "The Response of Ocular Pressure to Corticosteroids," *International Ophthalmology Clinics*, 1966; 6:929-989.

Scott, J.R. and W.J. Roff eds. "Permeability," *Handbook of Common Polymers*, Cleveland: CRC Press, 1971; 554-558.

Shields, Bruce M. "Glaucoma Filtering Procedures," *A Study Guide for Glaucoma*, Baltimore: Williams & Wilkins, 1982; 453-476.

Siebold, et al. *Prodrug*, 1989; 5:3.

Skalka, H.W. and Prchal, J.T. "Effect of Corticosteroids on Cataract Formation," *Archives of Ophthalmology*, 1980; 98(10):1773-1777.

Smith, T., et al. "Sustained-release subconjunctival 5-Fluorouracil," *Ophthalmic Surgery and Lasers*, Sep. 1996; 27(9):763-767.

Starr, M.S. "Further Studies on the Effect of Prostaglandin on Intraocular Pressure in the Rabbit," *Experimental Eye Research*, 1971; 11(2):170-177.

Stewart, W., et al. "Washout periods for brimonidine 0.2% and latanoprost 0.005%," *American Journal of Ophthalmology*, Jun. 2001; 131(6):798-799.

Taba, K.E., et al. "Intravitreal sustained release fluocinolone implant inhibits experimental choroidal neovascularization," *Investigative Ophthalmology & Visual Science*, Mar. 1999; 40(4):S172, abstract 920.

Takano, S.,et al. "Inhibition of Angiogenesis by a Novel Diaminoanthraquinone that Inhibits Protein Kinase C," *Molecular Biology of the Cell*, 1993; 4:358A, abstract 2076.

Tan, D.T.H., et al. "Randomized Clinical Trial of a New Dexamethasone Delivery System (Surodex) for Treating of Post-Cataract Surgery Inflammation," *Ophthalmology*, 1999; 106(2):223-231.

Tennant, J.L. "Cystoid maculopathy," *Current concepts in cataract surgery: selected proceedings of the fifth biennial cataract surgical congress*, Emery, J.M. ed. St. Louis: CV Mosby, 1978; 360-362.

Theng, J.T.S., et al. "Pharmacokinetic and Toxicity Study of an Intraocular Cyclosporine DDS in the Anterior Segment of Rabbit Eyes," *Investigative Ophthalmology & Visual Science*, Nov. 2003; 44(11):4895-4899.

Tracy, M.A., et al. "Factors affecting the degradation rate of poly(lactide-co-glycolide) microspheres in vivo and in vitro," *Biomaterials*, 1999; 20:1057-1062.

Tsubota, K. "Ocular Surface Management in Corneal Transplantation, A Review," *Japanese Journal of Ophthalmology*, 1999; 43(6):502-508.

Turcotte, J.G., et al. "Rejection Crises in Human Renal Transplant Recipients: Control with High Dose Methylprednisolone Therapy," *Archives of Surgery*, 1972; 105(1):230-236.

*The United States Pharmacopeia, The National Formulary*, "USP 23/NF 18," 1995; 1790-1798.

*The United States Pharmacopeia, The National Formulary*, "USP 24/NF 19," 2000; 1941-1951.

Watson, P., et al. "A Six-month, Randomized, Double-masked Study Comparing Latanoprost with Timolol in Open-angle Glaucoma and Ocular Hypertension," *Ophthalmology*, 1996; 103(1):126-137.

Weisbecker, C.A., et al., eds. *Physicians' Desk Reference for Ophthalmology 27th ed.*, Montvale, NJ: Medical Economics Company, 1998; 7-8, 278-279.

Wingate, R.J., et al. "Intravitreal Triamcinolone and Elevated Intraocular Pressure," *Australian and New Zealand Journal of Ophthalmology*, Dec. 1999; 27(6):431-2.

Woodward, D.F., et al. "AGN 192024 (Lumigan®): A Synthetic Prostamide Analog that Lowers Primate Intraocular Pressure by Virtue of Its Inherent Pharmacological Activity," *Investigative Ophthalmology & Visual Science*, 2002; 43, abstract 4110.

Woodward, D.F., et al. "The Pharmacology of Bimatoprost (Lumigan™)," *Survey of Ophthalmology*, 2001; 45(Suppl 4):S337-5345.

Wright, P.S., et al. "Inhibition of Angiogenesis In Vitro and In Ovo with an Inhibitor of Cellular Protein Kinases, MDL 27032," *Journal of Cellular Physiology*, 1992; 152(3):448-457.

Xu, J., et al. "Permeability and Diffusion in Vitreous Humor: Implications for Drug Delivery," *Pharmaceutical Research*, 2000; 17(6):664-669.

Zhou, T., et al. "Development of a Multiple-Drug Delivery Implant for Introcular Management of Proliferative Vitreoretinopathy," *Journal of Controlled Release*, 1998; 55:281-295.

* cited by examiner

Figure 11    Processes used for the manufacture of the DEX PS DDS
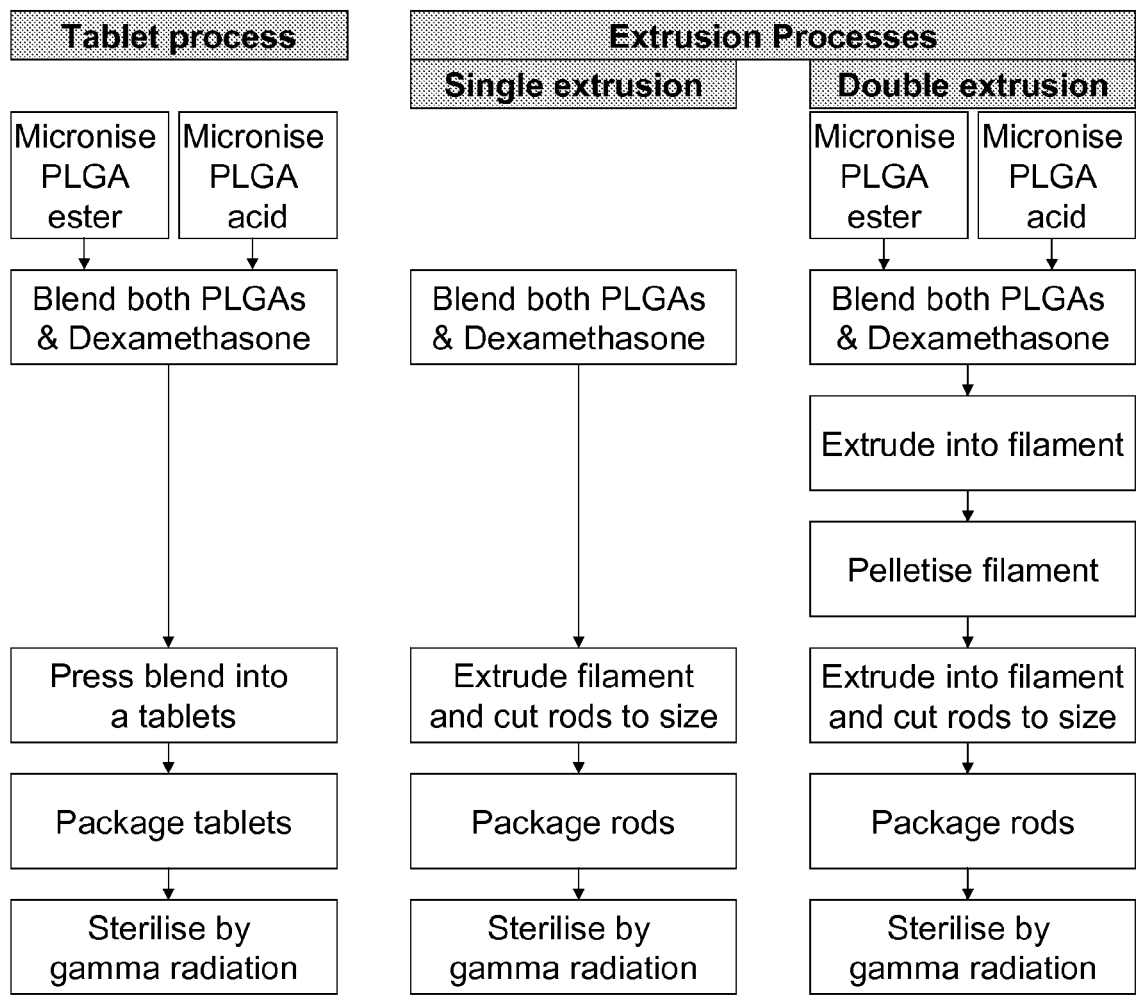

Figure 12 *In vitro* dexamethasone release rate comparison of two Lots of tabletted and single extruded DEX PS DDS
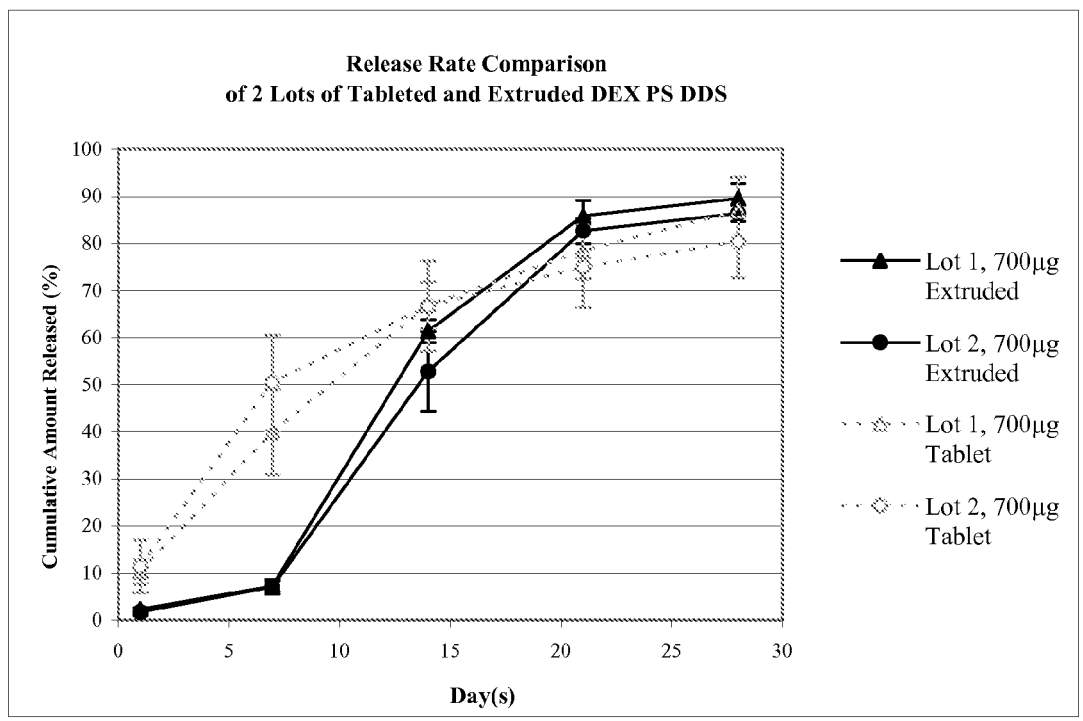

Figure 13. SEM pictures of tabletted and extruded DEX PS DDS
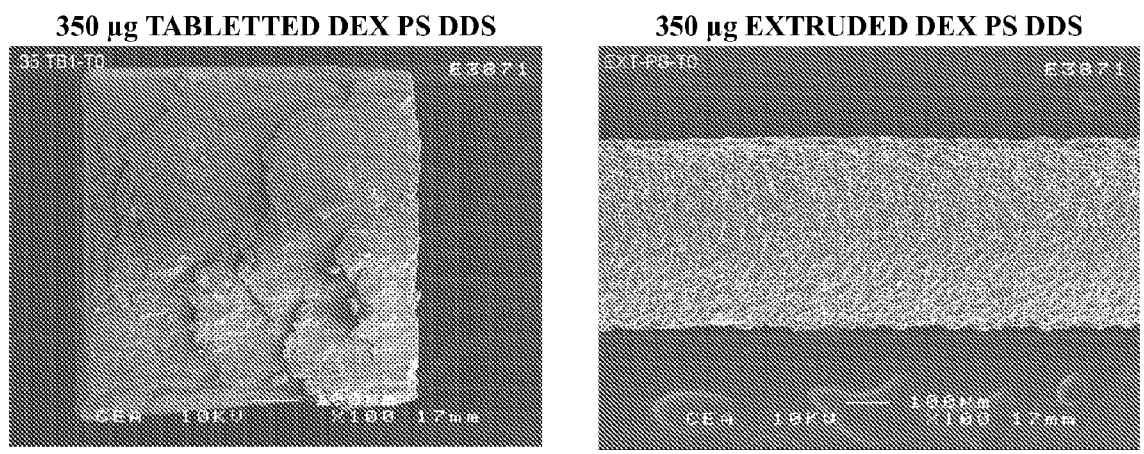

Figure 14    Content uniformity in DEX PS DDS after extrusion from batches made of milled and un-milled PLGAs
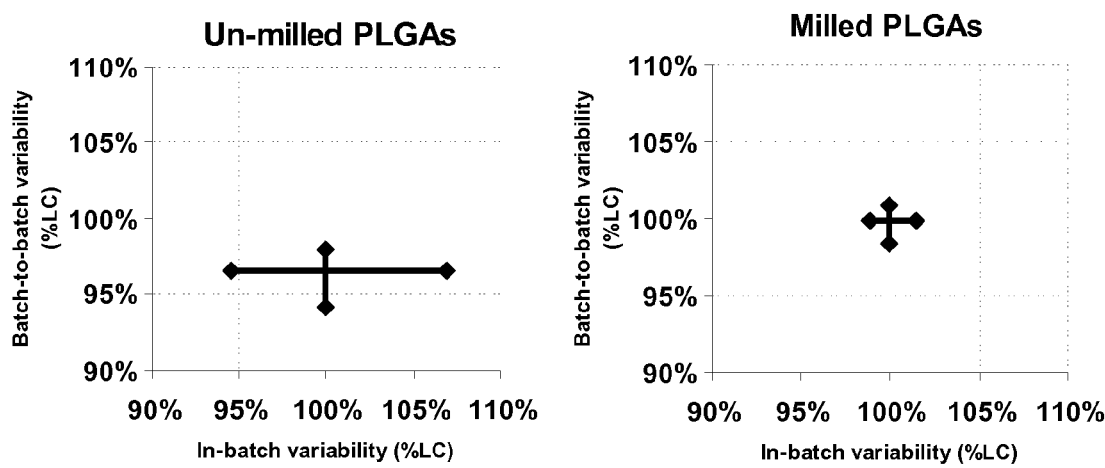

Figure 15    *In vitro* Release profile of DEX PS DDS manufactured by single and double extrusion.
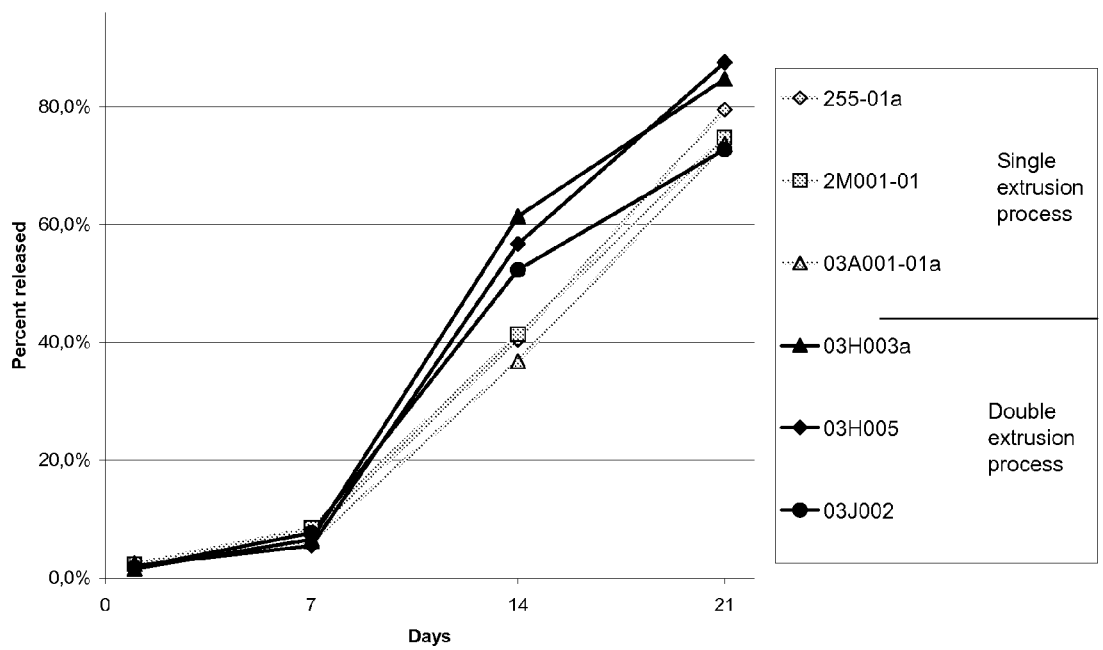

Figure 16    Flow diagram of double extrusion process for the manufacture of the DEX PS DDS
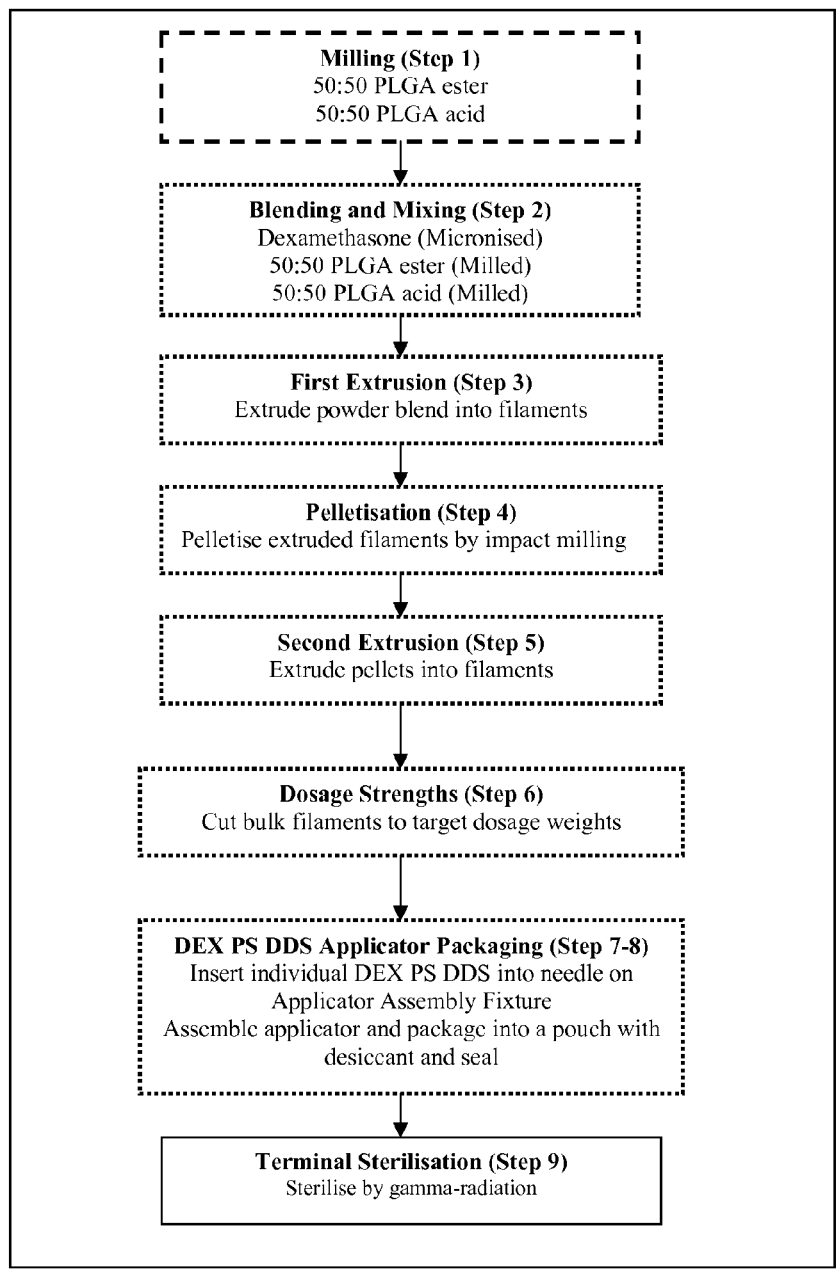

Figure 17  Cut-Away View of the DEX PS DDS Applicator System
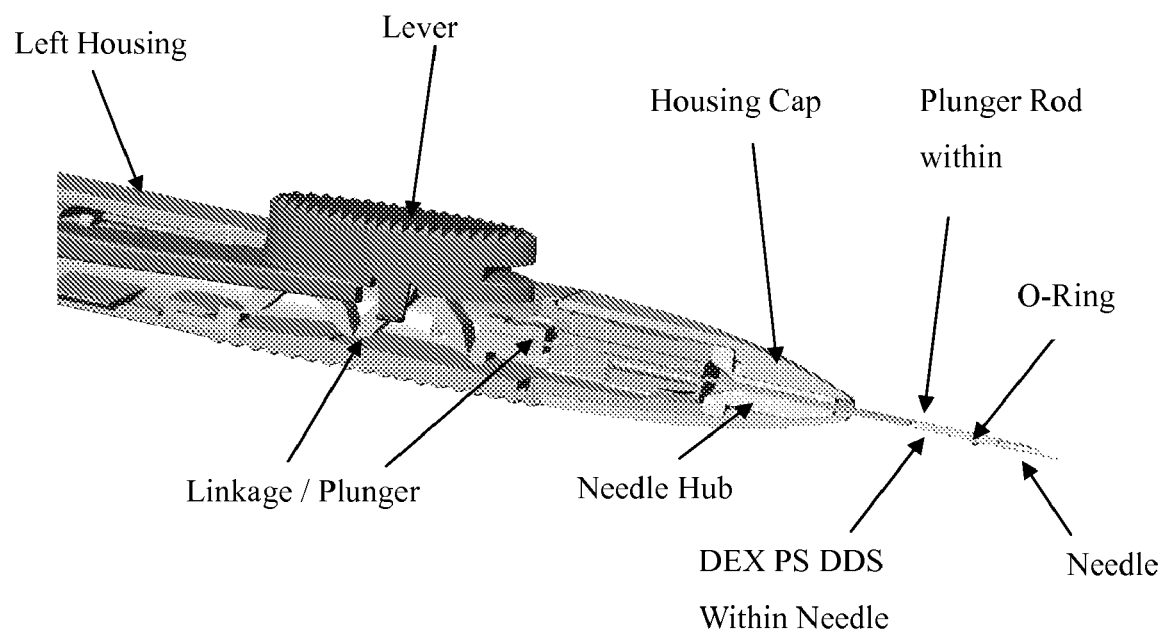

OCULAR IMPLANT MADE BY A DOUBLE EXTRUSION PROCESS

CROSS REFERENCE

This application is a continuation of U.S. patent application Ser. No. 10/918,597, filed Aug. 13, 2004, which a continuation in part of U.S. patent application Ser. No. 10/340,237, filed Jan. 9, 2003, the entire contents of which is incorporated herein by reference.

BACKGROUND

This invention relates to implants and methods for treating an ocular condition. In particular the present invention relates to implants and methods for treating an ocular condition by implanting into an ocular region or site a bioerodible implant comprising an active agent and a bioerodible polymer matrix, wherein the implant is made by a double extrusion process. The bioerodible implants of this invention have varying and extended release rates to provide for improved kinetics of release of one or more active (therapeutic) agents over time.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (behind the retina but in front of the posterior wall of the lens capsule), the lens or the lens capsule and blood vessels and nerve which vascularize or innervate an anterior ocular region or site. A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

The present invention is concerned with and directed to an implant and methods for the treatment of an ocular condition, such as an anterior ocular condition or a posterior ocular condition or to an ocular condition which can be characterized as both an anterior ocular condition and a posterior ocular condition.

Therapeutic compounds useful for the treatment of an ocular condition can include active agents with, for example, an anti-neoplastic, anti-angiogenesis, kinase inhibition, anticholinergic, anti-adrenergic and/or anti-inflammatory activity.

Macular degeneration, such as age related macular degeneration ("AMD") is a leading cause of blindness in the world. It is estimated that thirteen million Americans have evidence of macular degeneration. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied.

Macular edema is a non-specific response of the retina to a variety of insults. It is associated with a number of diseases, including uveitis, retinal vascular abnormalities (diabetic retinopathy and retinal vein occlusive disease), a sequelae of cataract surgery (post-cataract cystoid macular oedema), macular epiretinal membranes, and inherited or acquired retinal degeneration. Macular edema involves the breakdown of the inner blood retinal barrier at the level of the capillary endothelium, resulting in abnormal retinal vascular permeability and leakage into the adjacent retinal tissues. The macula becomes thickened due to fluid accumulation resulting in significant disturbances in visual acuity (Ahmed I, Ai E. Macular disorders: cystoid macular oedema. In: Yanoff M, Duker J S, eds. Ophthalmology. London: Mosby; 1999:34; Dick J, Jampol L M, Haller J A. Macular edema. In: Ryan S, Schachat A P, eds. Retina. 3rd ed. St. Louis, Mo.: CV Mosby; 2001, v2, Section 2 chap 57:967-979).

Macular edema may occur in diseases causing cumulative injury over many years, such as diabetic retinopathy, or as a result of more acute events, such as central retinal vein occlusion or branch retinal vein occlusion.

In some cases macular edema resolves spontaneously or with short-term treatment. Therapeutic choices for macular oedema depend on the cause and severity of the condition. Currently there are no approved pharmacological therapies for macular edema. Focal/grid laser photocoagulation has been shown to be efficacious in the prevention of moderate visual loss for macular oedema due to diabetic retinopathy (Akduman L, Olk R S. The early treatment diabetic retinopathy study. In: Kertes P S, Conway M D, eds. Clinical trials in ophthalmology: a summary and practice guide. Baltimore, Md.: Lippincott Williams & Wilkins; 1998:15-35; Frank R N. Etiologic mechanisms in diabetic retinopathy. In: Ryan S, Schachat A P, eds. Retina. 3rd ed. St. Louis, Mo.: CV Mosby; 2001, v2, Section 2, chap 71:1259-1294). Argon laser photocoagulation increased the likelihood of vision improvement in patients with macular oedema due to branch retinal vein occlusion (BRVO) (Orth D. The branch vein occlusion study. In: Kertes P, Conway M, eds. Clinical trials in ophthalmology: a summary and practice guide. Baltimore, Md.: Lippincott Williams & Wilkins; 1998:113-127; Fekrat S, Finkelstein D. The Central Vein Occlusion Study. In: Kertes P S, Conway M D, eds. Clinical trials in ophthalmology: a summary and practice guide. Baltimore, Md.: Lippincott Williams & Wilkins; 1998:129-143), but not in patients with macular oedema due to central retinal vein occlusion (CRVO) (Fekrat and Finkelstein 1998, supra; Clarkson J G Central retinal vein occlusion. In: Ryan S, Schachat A P, eds. Retina. 3rd ed. St. Louis, Mo.: CV Mosby; 2001, v2, chap 75:1368-1375). For CRVO, there are no known effective therapies.

An anti-inflammatory (i.e. immunosuppressive) agent can be used for the treatment of an ocular condition, such as a posterior ocular condition, which involves inflammation, such as an uveitis or macular edema. Thus, topical or oral glucocorticoids have been used to treat uveitis. A major problem with topical and oral drug administration is the inability of the drug to achieve an adequate (i.e. therapeutic) intraocular concentration. See e.g. Bloch-Michel E. (1992). *Opening address: intermediate uveitis*, In Intermediate Uveitis, Dev. Ophthalmol, W. R. F. Böke et al. editors, Basel: Karger, 23:1-2; Pinar, V., et al. (1997). *Intraocular inflammation and uveitis*" In Basic and Clinical Science Course. Section 9 (1997-1998) San Francisco: American Academy of Ophthalmology, pp. 57-80, 102-103, 152-156; Böke, W. (1992). *Clinical picture of intermediate uveitis*, In Intermediate Uveitis, Dev. Ophthalmol. W. R. F. Böke et al. editors, Basel: Karger, 23:20-7; and Cheng C-K et al. (1995). *Intravitreal sustained-release dexamethasone device in the treatment of experimental uveitis*, Invest. Ophthalmol. Vis. Sci. 36:442-53.

Systemic glucocorticoid administration can be used alone or in addition to topical glucocorticoids for the treatment of uveitis. However, prolonged exposure to high plasma concentrations (administration of 1 mg/kg/day for 2-3 weeks) of steroid is often necessary so that therapeutic levels can be achieved in the eye.

Unfortunately, these high drug plasma levels commonly lead to systemic side effects such as hypertension, hyperglycemia, increased susceptibility to infection, peptic ulcers, psychosis, and other complications. Cheng C-K et al. (1995). *Intravitreal sustained-release dexamethasone device in the treatment of experimental uveitis*, Invest. Ophthalmol. Vis. Sci. 36:442-53; Schwartz, B. (1966). *The response of ocular pressure to corticosteroids*, Ophthalmol. Clin. North Am. 6:929-89; Skalka, H. W. et al. (1980). *Effect of corticosteroids on cataract formation*, Arch Ophthalmol 98:1773-7; and Renfro, L. et al. (1992). *Ocular effects of topical and systemic steroids*, Dermatologic Clinics 10:505-12.

Additionally, delivery to the eye of a therapeutic amount of an active agent can be difficult, if not impossible, for drugs with short plasma half-lives since the exposure of the drug to intraocular tissues is limited. Therefore, a more efficient way of delivering a drug to treat a posterior ocular condition is to place the drug directly in the eye, such as directly into the vitreous. Maurice, D. M. (1983). *Micropharmaceutics of the eye*, Ocular Inflammation Ther. 1:97-102; Lee, V. H. L. et al. (1989). *Drug delivery to the posterior segment*" Chapter 25 In Retina. T. E. Ogden and A. P. Schachat eds., St. Louis: C V Mosby, Vol. 1, pp. 483-98; and Olsen, T. W. et al. (1995). *Human scleral permeability: effects of age, cryotherapy, transscleral diode laser, and surgical thinning*, Invest. Ophthalmol. Vis. Sci. 36:1893-1903.

Techniques such as intravitreal injection of a drug have shown promising results, but due to the short intraocular half-life of active agent, such as glucocorticoids (approximately 3 hours), intravitreal injections must be frequently repeated to maintain a therapeutic drug level. In turn, this repetitive process increases the potential for side effects such as retinal detachment, endophthalmitis, and cataracts. Maurice, D. M. (1983). *Micropharmaceutics of the eye*, Ocular Inflammation Ther. 1:97-102; Olsen, T. W. et al. (1995). *Human scleral permeability: effects of age, cryotherapy, transscleral diode laser, and surgical thinning*, Invest. Ophthalmol. Vis. Sci. 36:1893-1903; and Kwak, H. W. and D'Amico, D. J. (1992). *Evaluation of the retinal toxicity and pharmacokinetics of dexamethasone after intravitreal injection*, Arch. Ophthalmol. 110:259-66.

Additionally, topical, systemic, and periocular glucocorticoid treatment must be monitored closely due to toxicity and the long-term side effects associated with chronic systemic drug exposure sequelae. Rao, N. A. et al. (1997). *Intraocular inflammation and uveitis*, In Basic and Clinical Science Course. Section 9 (1997-1998) San Francisco: American Academy of Ophthalmology, pp. 57-80, 102-103, 152-156; Schwartz, B. (1966). *The response of ocular pressure to corticosteroids, Ophthalmol Clin North Am* 6:929-89; Skalka, H. W. and Pichal, J. T. (1980). *Effect of corticosteroids on cataract formation*, Arch Ophthalmol 98:1773-7; Renfro, L and Snow, J. S. (1992). *Ocular effects of topical and systemic steroids*, Dermatologic Clinics 10:505-12; Bodor, N. et al. (1992). *A comparison of intraocular pressure elevating activity of loteprednol etabonate and dexamethasone in rabbits*, Current Eye Research 11:525-30.

U.S. Pat. No. 6,217,895 discusses a method of administering a corticosteroid to the posterior segment of the eye, but does not disclose a bioerodible implant.

U.S. Pat. No. 5,501,856 discloses controlled release pharmaceutical preparations for intraocular implants to be applied to the interior of the eye after a surgical operation for disorders in retina/vitreous body or for glaucoma.

U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. As shown by in vitro testing of the drug release kinetics, the 100-120 μg 50/50 PLGA/dexamethasone implant disclosed did not show appreciable drug release until the beginning of the fourth week, unless a release enhancer, such as HPMC was added to the formulation.

U.S. Pat. No. 5,824,072 discloses implants for introduction into a suprachoroidal space or an avascular region of the eye, and describes a methylcellulose (i.e. non-biodegradable) implant comprising dexamethasone. WO 9513765 discloses implants comprising active agents for introduction into a suprachoroidal or an avascular region of an eye for therapeutic purposes.

U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana. U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR). Zhou, T, et al. (1998). *Development of a multiple-drug delivery implant for intraocular management of proliferative vitreoretinopathy*, Journal of Controlled Release 55: 281-295.

U.S. Pat. No. 6,046,187 discusses methods and compositions for modulating local anesthetic by administering one or more glucocorticosteroid agents before, simultaneously with or after the administration of a local anesthetic at a site in a patient.

U.S. Pat. No. 3,986,510 discusses ocular inserts having one or more inner reservoirs of a drug formulation confined within a bioerodible drug release rate controlling material of a shape adapted for insertion and retention in the "sac of the eye," which is indicated as being bounded by the surfaces of the bulbar conjunctiva of the sclera of the eyeball and the palpebral conjunctiva of the eyelid, or for placement over the corneal section of the eye.

U.S. Pat. No. 6,369,116 discusses an implant with a release modifier inserted in a scleral flap.

EP 0 654256 discusses use of a scleral plug after surgery on a vitreous body, for plugging an incision.

U.S. Pat. No. 4,863,457 discusses the use of a bioerodible implant to prevent failure of glaucoma filtration surgery by positioning the implant either in the subconjunctival region between the conjunctival membrane overlying it and the sclera beneath it or within the sclera itself within a partial thickness sclera flap.

EP 488 401 discusses intraocular implants, made of certain polylactic acids, to be applied to the interior of the eye after a surgical operation for disorders of the retina/vitreous body or for glaucoma.

EP 430539 discusses use of a bioerodible implant which is inserted in the suprachoroid.

U.S. Pat. No. 6,726,918 discusses implants for treating inflammation mediated conditions of the eye.

Significantly, it is known that PLGA co-polymer formulations of a bioerodible polymer comprising an active agent typically release the active agent with a characteristic sigmoidal release profile (as viewed as time vs percent of total active agent released), that is after a relatively long initial lag period (the first release phase) when little if any active agent is released, there is a high positive slope period when most of the active agent is released (the second release phase) followed by another near horizontal (third) release phase, when the drug release reaches a plateau.

One of the alternatives to intravitreal injection to administer drugs is the placement of biodegradable implants under the sclera or into the subconjunctival or suprachoroidal space, as described in U.S. Pat. No. 4,863,457 to Lee; WO 95/13765 to Wong et al.; WO 00/37056 to Wong et al.; EP 430,539 to Wong; in Gould et al., *Can. J. Ophthalmol.* 29(4):168-171 (1994); and in Apel et al., *Curr. Eye Res.* 14:659-667 (1995).

Furthermore, the controlled release of drugs from polylactide/polyglycolide (PLGA) copolymers into the vitreous has been disclosed, e.g., in U.S. Pat. No. 5,501,856 to Ohtori et al. and EP 654,256 to Ogura.

Recent experimental work has demonstrated that uncapped PLGA degrades faster than capped (end-capped) PLGA (Park et al., *J. Control. Rel.* 55:181-191 (1998); Tracy et al., *Biomaterials* 20:1057-1062 (1999); and Jong et al., *Polymer* 42:2795-2802 (2001). Accordingly, implants containing mixtures of uncapped and capped PLGA have been formed to modulate drug release. For example, U.S. Pat. No. 6,217,911 to Vaughn et al. ('911) and U.S. Pat. No. 6,309,669 to Setterstrom et al. ('669) disclose the delivery of drugs from a blend of uncapped and capped PLGA copolymer to curtail initial burst release of the drugs. In the '911 patent, the composition delivers non-steroidal anti-inflammatory drugs from PLGA microspheres made by a solvent extraction process or PLGA microcapsules prepared by a solvent evaporation process over a duration of 24 hours to 2 months. In the '669 patent, the composition delivers various pharmaceuticals from PLGA microcapsules over a duration of 1-100 days. The PLGA microspheres or microcapsules are administered orally or as an aqueous injectable formulation. As mentioned above, there is poor partitioning of drug into the eye with oral administration. Furthermore, use of an aqueous injectable drug composition (for injecting into the eye) should be avoided since the eye is a closed space (limited volume) with intraocular pressure ranges that are strictly maintained. Administration of an injectable may increase intraocular volume to a point where intraocular pressures would then become pathologic.

Potent corticosteroids such as dexamethasone suppress inflammation by inhibiting edema, fibrin deposition, capillary leakage and phagocytic migration, all key features of the inflammatory response. Corticosteroids prevent the release of prostaglandins, some of which have been identified as mediators of cystoid macular oedema (Leopold I H. Nonsteroidal and steroidal anti-inflammatory agents. In: Sears M, Tarkkanen A, eds. Surgical pharmacology of the eye. New York, N.Y.: Raven Press; 1985:83-133; Tennant J L. Cystoid maculopathy: 125 prostaglandins in ophthalmology. In: Emery J M, ed. Current concepts in cataract surgery: selected proceedings of the fifth biennial cataract surgical congress, Section 3. St. Louis, Mo.: C V Mosby; 1978; 360-362). Additionally, corticosteroids including dexamethasone have been shown to inhibit the expression of vascular endothelial growth factor (VEGF), a cytokine which is a potent promoter of vascular permeability (Nauck M, Karakiulakis G, Perruchoud A P, Papakonstantinou E, Roth M. Corticosteroids inhibit the expression of the vascular endothelial growth factor gene in human vascular smooth muscle cells. Eur J Pharmacol 1998; 341:309-315).

The use of dexamethasone to date, by conventional routes of administration, has yielded limited success in treating retinal disorders, including macular oedema, largely due to the inability to deliver and maintain adequate quantities of the drug to the posterior segment without resultant toxicity. After topical administration of dexamethasone, only about 1% reaches the anterior segment, and only a fraction of that amount moves into the posterior segment (Lee V H L, Pince K J, Frambach D A, Martini B. Drug delivery to the posterior segment. In: Ogden T E, Schachat A P, eds. Retina. St. Louis, Mo.: C V Mosby, 1989, chap 25:483-498). Although intravitreal injections of dexamethasone have been used, the exposure to the drug is very brief as the half-life of the drug within the eye is approximately 3 hours (Peyman G A, Herbst R. Bacterial endophthalmitis. Arch Ophthalmol 1974; 91:416-418). Periocular and posterior sub-Tenon's injections of dexamethasone also have a short term treatment effect (Riordan-Eva P, Lightman S. Orbital floor steroid injections in the treatment of uveitis. Eye 1994; 8 (Pt 1):66-69; Jennings T, Rusin M, Tessler H, Cunha-Vaz J. Posterior sub-Tenon's injections of corticosteroids in uveitis patients with cystoid macular edema. Jpn J Ophthalmol 1988; 32:385-391).

Adverse reactions listed for conventional ophthalmic dexamethasone preparations include: ocular hypertension, glaucoma, posterior subcapsular cataract formation, and secondary ocular infection from pathogens including herpes simplex (Lee et al, 1989 supra; Skalka H W, Prchal J T. Effect of corticosteroids on cataract formation. Arch Ophthalmol 1980; 98:1773-1777; Renfro L, Snow J S. Ocular effects of topical and systemic steroids. Dermatol Clin 1992; 10(3): 505-512; Physician's Desk Reference, 2003). Systemic doses are associated with additional hazardous side-effects including hypertension, hyperglycemias, increased susceptibility to infection, and peptic ulcers (Physician's Desk Reference, 2003).

By delivering a drug directly into the vitreous cavity, blood eye barriers can be circumvented and intraocular therapeutic levels can be achieved with minimal risk of systemic toxicity (Lee et al, 1989 supra). This route of administration typically results in a short half-life unless the drug can be delivered using a formulation capable of providing sustained release.

Consequently, a biodegradable implant for delivering a therapeutic agent to an ocular region may provide significant medical benefit for patients afflicted with a medical condition of the eye.

DRAWINGS

Figure 9:
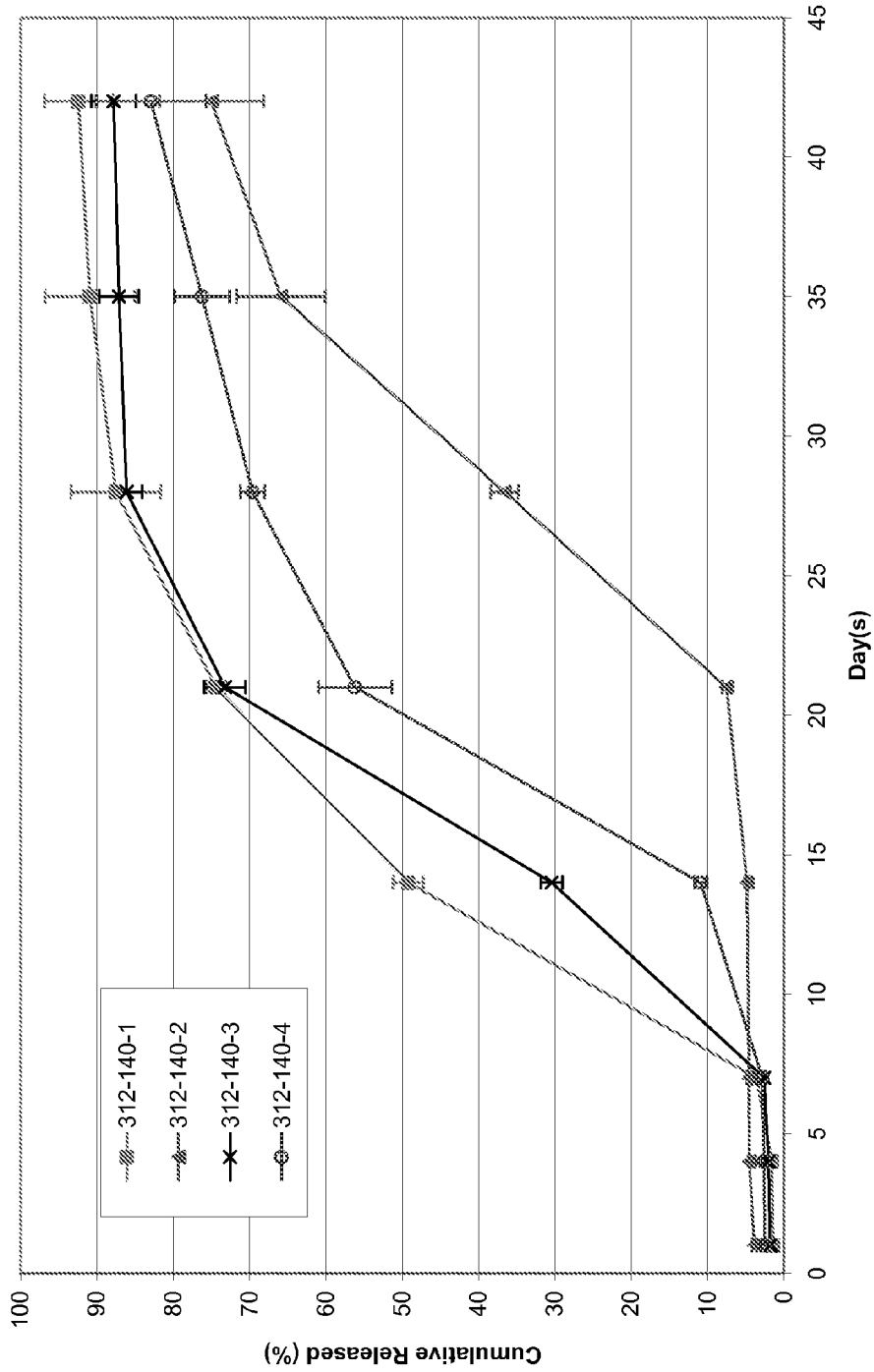

FIG. 9 shows the in vitro total cumulative percentage release of dexamethasone into a saline solution at 37° C. from 60/40 w/w dexamethasone/PLGA implants having a weight ratio of 40:0 hydrophobic end to hydrophilic end PLGA (312-140-2), weight ratio of 30:10 hydrophobic end to hydrophilic end PLGA (312-140-4), weight ratio of 20:20 hydrophobic end to hydrophilic end PLGA (312-140-3), and weight ratio of 0:40 hydrophobic end to hydrophilic end PLGA (312-140-1).

Figure 10:
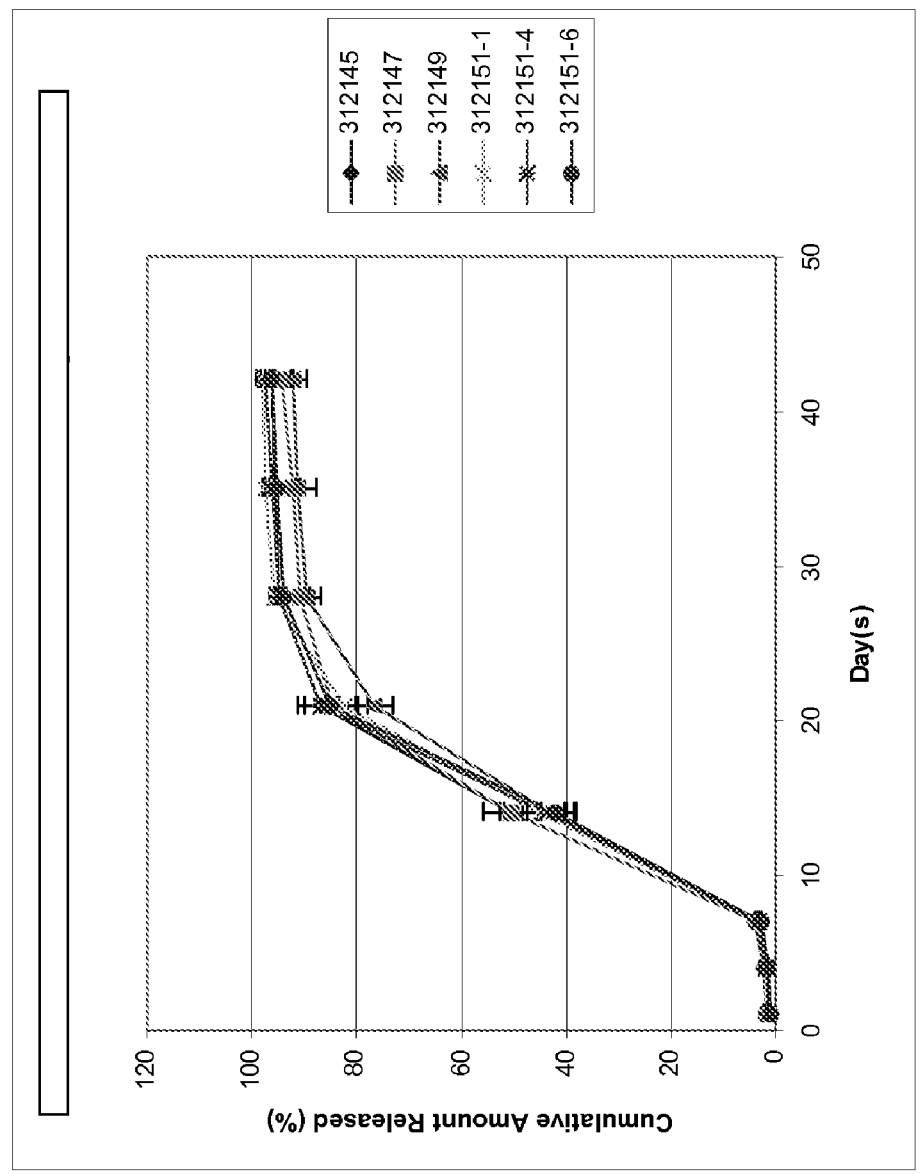

FIG. 10 compares the in vitro cumulative percentage release of dexamethasone into a saline solution at 37° C. for six lots of extruded implants having 60% by weight dexamethasone, 30% by weight hydrophilic end PLGA, and 10% by weight hydrophobic end PLGA.

FIG. 11 is a flow chart illustrating manufacturing processes for tablet, single and double extrusion methods for making an ocular implant within the scope of the present invention.

FIG. 12 is a graph which shows the cumulative amount of dexamethasone released in vitro over time for an ocular implant made by either tabletting or a single extrusion processes.

FIG. 13 are scanning electromicrographs (SEM) pictures of DEX PS DDS implants made by a tabletting process and by a single extrusion process.

FIG. 14 shows two graphs of batch to batch vs within batch variability of % LC (% of total dexamethasone) for implants made from either unmilled or milled PLGAs.

FIG. 15 is a graph showing in vitro release of dexamethasone from DEX PS DDS implants made by either a single extrusion or by a double extrusion process.

FIG. 16 is a flow chart illustrating a double extrusion manufacturing processes for making an ocular implant within the scope of the present invention.

FIG. 17 provides a cut-away side view of an applicator to implant an ocular implant within the scope of the present invention.

SUMMARY

Definitions

The following terms as used herein have the following meanings:

"About" means approximately or nearly and in the context of a numerical value or range set forth herein means ±10% of the numerical value or range recited or claimed.

"Active agent" and "drug" are used interchangeably and refer to any substance used to treat an ocular condition.

"Bioerodible polymer" means a polymer which degrades in vivo, and wherein erosion of the polymer over time is required to achieve the active agent release kinetics according to the present invention. Thus, hydrogels such as methylcellulose which act to release drug through polymer swelling are specifically excluded from the term "bioerodible (or biodegradable) polymer". The words "bioerodible" and "biodegradable" are synonymous and are used interchangeably herein.

"Concentration equivalent to dexamethasone", or "dexamethasone equivalent" means a concentration of an active agent, such as a steroidal anti-inflammatory agent, necessary to have approximately the same efficacy in vivo as a particular dose of dexamethasone. For example, hydrocortisone is approximately twenty five fold less potent than dexamethasone, and thus a 25 mg dose of hydrocortisone would be equivalent to a 1 mg dose of dexamethasone. One of ordinary skill in the art would be able to determine the concentration equivalent to dexamethasone for a particular steroidal anti-inflammatory agent from one of several standard tests known in the art. Relative potencies of selected corticosteroids may be found, for example, in Gilman, A. G., et al., eds. (1990). *Goodman and Gilman's: The Pharmacological Basis of Therapeutics*. 8th Edition, Pergamon Press: New York, p. 1447.

"Cumulative release profile" means to the cumulative total percent of an active agent released from an implant into an ocular region or site in vivo over time or into a specific release medium in vitro over time.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation.

"Measured under infinite sink conditions in vitro," means assays to measure drug release in vitro, wherein the experiment is designed such that the drug concentration in the receptor medium never exceeds 5% of saturation. Examples of suitable assays may be found, for example, in USP 23; NF 18 (1995) pp. 1790-1798.

"Ocular condition" means a disease, aliment or condition which affects or involves the eye or one or the parts or regions of the eye, such as a retinal disease. The eye includes the eyeball and the tissues and fluids which constitute the eyeball, the periocular muscles (such as the oblique and rectus muscles) and the portion of the optic nerve which is within or adjacent to the eyeball. "Ocular condition" is synonymous with "medical condition of the eye".

"Plurality" means two or more.

"Posterior ocular condition" means a disease, ailment or condition which affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Steroidal anti-inflammatory agent" and "glucocorticoid" are used interchangeably herein, and are meant to include steroidal agents, compounds or drugs which reduce inflammation when administered at a therapeutically effective level.

"Substantially" in relation to the release profile or the release characteristic of an active agent from a bioerodible implant as in the phrase "substantially continuous rate" of the active agent release rate from the implant means, that the rate of release (i.e. amount of active agent released/unit of time) does not vary by more than 100%, and preferably does not vary by more than 50%, over the period of time selected (i.e. a number of days). "Substantially" in relation to the blending, mixing or dispersing of an active agent in a polymer, as in the phrase "substantially homogenously dispersed" means that there are no or essentially no particles (i.e. aggregations) of active agent in such a homogenous dispersal.

"Suitable for insertion (or implantation) in (or into) an ocular region or site" with regard to an implant, means an implant which has a size (dimensions) such that it can be inserted or implanted without causing excessive tissue damage and without unduly physically interfering with the existing vision of the patient into which the implant is implanted or inserted.

"Therapeutic levels" or "therapeutic amount" means an amount or a concentration of an active agent that has been locally delivered to an ocular region that is appropriate to safely treat an ocular condition so as to reduce or prevent a symptom of an ocular condition.

The meaning of abbreviations used herein is explained below:

| Term | Meaning |
| --- | --- |
| $1^H$-NMR | Proton nuclear magnetic resonance |
| ABS | Poly acrylonitrile butadiene styrene |
| ACC | Anterior chamber cell |
| ALT | Alanine aminotransferase |
| API | Active pharmaceutical ingredient |
| AVC | Anterior vitreous cells |
| BCVA | Best-corrected visual acuity |
| BI | Boehringer Ingelheim |
| BRVO | Branch retinal vein occlusion |
| BSE | Bovine Spongiform Encephalopathy |
| BVOS | Branch Vein Occlusion Study |
| B/N | Batch number |
| ° C. | Degrees Centigrade |
| CA | California |
| CAS | Chemical abstract services |
| CF | Count fingers |
| CFU | Colony forming unit |
| cGMP | Current Good Manufacturing Practice |
| CI | Confidence interval |
| CIB | Clinical Investigator's Brochure |
| $CO_2$ | Carbon dioxide |
| COEX | Co-extruded |
| CRVO | Central retinal vein occlusion |

-continued

| Term | Meaning |
|---|---|
| CVOS | Central Vein Occlusion Study |
| DDS | Drug delivery system |
| DEX | Dexamethasone |
| DEX PS DDS | Dexamethasone posterior segment drug delivery system (implant) |
| DEX PS DDS Applicator system | Dexamethasone posterior segment drug delivery Applicator system (medicinal product) |
| DME | Diabetic macular oedema |
| EMEA | European medicine evaluation agency |
| ETDRS | Early Treatment of Diabetic Retinopathy Study |
| EU | Endotoxin unit |
| ° F. | Degrees Fahrenheit |
| G | Gram |
| GLP | Good Laboratory Practice |
| GRB | Geographical BSE (Bovine Spongiform Encephalopathies) risk |
| $H_2O$ | Water |
| HDPE | High density polyethylene |
| HPLC | High performance liquid chromatography |
| IEC | Independent Ethics Committee |
| IMPD | Investigational medicinal product dossier |
| INN | International Non-proprietary Name |
| IOP | Intraocular pressure |
| IPC | In process control |
| IR | Infrared |
| IRB | Institutional Review Board |
| ISO | International standard organisation |
| Kg | Kilogram |
| kGy | Kilo Grey |
| LAF | Laminar Air Flow |
| LAL | Limulus Amebocytes Lysate |
| LC | Label Claim |
| LOCF | Last observation carried forward |
| LS | Label strength |
| ME | Macular oedema |
| μg | Microgram |
| Mg | Milligram |
| μJ | Microjoules |
| mL | Millilitre(s) |
| Mm | Millimetre(s) |
| mmHg | Millimeters of mercury |
| mol | Mole |
| n or N | Number |
| n/a | Not applicable |
| ND | Not detected |
| Ng | Nanogram(s) |
| NSAID | Nonsteroidal anti-inflammatory drug |
| NT | Not tested |
| OCT | Optical Coherence Tomography |
| PDE | Permitted daily exposure |
| PET | Polyethylene terephthalate |
| pH | Hydrogen potential |
| Ph. Eur. | European Pharmacopoeia |
| PK | Pharmacokinetics |
| pKa | Acid dissociation constant |
| PLGA, PLG | Poly (D,L-lactide-co-glycolide). |
| PME | Persistent macular edema |
| ppm | Part per million |
| PS | Posterior segment |
| PVR | Proliferative vitreoretinopathy |
| RH | Relative humidity |
| SAE | Serious adverse event |
| SD | Standard deviation |
| SEM | Scanning electron microscope |
| TSE | Transmissible spongiform encephalopathy |
| USA | United States of America |
| USP | United States Pharmacopoeia |
| UV | Ultra violet |
| VEGF | Vascular endothelial growth factor |
| WPE | Ultrahigh molecular weight polyethylene |

Our invention encompasses a bioerodible implant for treating a medical condition of the eye comprising an active agent dispersed within a biodegradable polymer matrix, wherein at least about 75% of the particles of the active agent have a diameter of less than about 10 μm. Preferably, at least about 99% of the particles have a diameter of s than about 20 μm.

The active agent can be selected from the group consisting of ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, steroids (such as a steroidal anti-inflammatory agent), antihypertensives, pressors, antibacterials, antivirals, antifungals, antiprotozoals, anti-infective agents, antitumor agents, antimetabolites, and antiangiogenic agents. Thus, the active agent can be cortisone, dexamethasone, fluocinolone, hydrocortisone, methylprednisolone, prednisolone, prednisone, triamcinolone, and any derivative thereof.

The bioerodible implant is sized for implantation in an ocular region. The ocular region can be any one or more of the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

An alternate embodiment of the bioerodible implant can comprise a steroid active agent dispersed within a biodegradable polymer matrix, wherein at least about 75% of the particles of the active agent have a diameter of less than about 20 μm.

Our present invention also encompasses a method for making a bioerodible implant for treating a medical condition of the eye, the method comprising a plurality of extrusions of a biodegradable polymer. This method can also comprise the step of milling the biodegradable polymer prior to the extrusion. The biodegradable polymer can be a poly(lactic-co-glycolic)acid (PLGA) copolymer. The ratio of lactic to glycolic acid monomers in the polymer can be about 50/50 weight percentage. Additionally, the PLGA copolymer can be about 20 to about 90 weight percent of the bioerodible implant. Alternately, the PLGA copolymer can be about 40 percent by weight of the bioerodible implant.

A detailed method for making a bioerodible implant for treating a medical condition of the eye can have the steps of: (a) milling a biodegradable polymer; (b) blending the milled biodegradable polymer and particles of an active agent, to thereby obtain a blended mixture of the milled biodegradable polymer and the particles of the active agent, wherein at least about 75% of the particles of the active agent have a diameter of less than about 20 μm; (c) carrying out a first extrusion of the blended mixture, to thereby obtain a first extrusion product; (d) pelletizing the first extrusion product, and; (e) carrying out a second extrusion of the pelletized first extrusion product, thereby obtaining a bioerodible implant for treating a medical condition of the eye. Our invention also includes a bioerodible implant for treating a medical condition of the eye made by this detailed method.

DESCRIPTION

The present invention provides biodegradable ocular implants and methods for treating medical conditions of the eye. Usually, the implants are formed to be monolithic, i.e., the particles of active agent are distributed throughout the biodegradable polymer matrix. Furthermore, the implants are formed to release an active agent into an ocular region of the eye over various time periods. The active agent may be release over a time period including, but is not limited to, approximately six months, approximately three months, approximately one month, or less than one month.

Biodegradable Implants for Treating Medical Conditions of the Eye

The implants of the invention include an active agent dispersed within a biodegradable polymer. The implant compositions typically vary according to the preferred drug release profile, the particular active agent used, the condition being treated, and the medical history of the patient. Active agents that may be used include, but are not limited to, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, and antiangiogenic agents.

In one variation the active agent is methotrexate. In another variation, the active agent is retinoic acid. In a preferred variation, the anti-inflammatory agent is a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a more preferred variation, the anti-inflammatory agent is a steroidal anti-inflammatory agent.

Steroidal Anti-Inflammatory Agents

The steroidal anti-inflammatory agents that may be used in the ocular implants include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one variation, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the biodegradable implant includes a combination of two or more steroidal anti-inflammatory agents.

The steroidal anti-inflammatory agent may constitute from about 10% to about 90% by weight of the implant. In one variation, the agent is from about 40% to about 80% by weight of the implant. In a preferred variation, the agent comprises about 60% by weight of the implant.

The Biodegradable Polymer Matrix

In one variation, the active agent may be homogeneously dispersed in the biodegradable polymer matrix of the implants. The selection of the biodegradable polymer matrix to be employed will vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% by weight of the implant.

Biodegradable polymer matrices which may be employed include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers may be crosslinked or non-crosslinked. If crosslinked, they are usually not more than lightly crosslinked, and are less than 5% crosslinked, usually less than 1% crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano, and amino. An exemplary list of biodegradable polymers that may be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In a preferred variation, a 50/50 PLGA copolymer is used. More preferably, a random copolymer of 50/50 PLGA is used.

Biodegradable polymer matrices that include mixtures of hydrophilic and hydrophobic ended PLGA may also be employed, and are useful in modulating polymer matrix degradation rates. Hydrophobic ended (also referred to as capped or end-capped) PLGA has an ester linkage hydrophobic in nature at the polymer terminus. Typical hydrophobic end groups include, but are not limited to alkyl esters and aromatic esters. Hydrophilic ended (also referred to as uncapped) PLGA has an end group hydrophilic in nature at the polymer terminus. PLGA with a hydrophilic end groups at the polymer terminus degrades faster than hydrophobic ended PLGA because it takes up water and undergoes hydrolysis at a faster rate (Tracy et al., *Biomaterials* 20:1057-1062 (1999)). Examples of suitable hydrophilic end groups that may be incorporated to enhance hydrolysis include, but are not limited to, carboxyl, hydroxyl, and polyethylene glycol. The specific end group will typically result from the initiator employed in the polymerization process. For example, if the initiator is water or carboxylic acid, the resulting end groups will be carboxyl and hydroxyl. Similarly, if the initiator is a monofunctional alcohol, the resulting end groups will be ester or hydroxyl.

The implants may be formed from all hydrophilic end PLGA or all hydrophobic end PLGA. In general, however, the ratio of hydrophilic end to hydrophobic end PLGA in the biodegradable polymer matrices of this invention range from about 10:1 to about 1:10 by weight. For example, the ratio may be 3:1, 2:1, or 1:1 by weight. In a preferred variation, an implant with a ratio of hydrophilic end to hydrophobic end PLGA of 3:1 w/w is used.

Additional Agents

Other agents may be employed in the formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The biodegradable ocular implants may also include additional hydrophilic or hydrophobic compounds that accelerate or retard release of the active agent. Furthermore, the inventors believe that because hydrophilic end PLGA has a higher degradation rate than hydrophobic end PLGA due to its ability to take up water more readily, increasing the amount of hydrophilic end PLGA in the implant polymer matrix will result in faster dissolution rates. FIG. 9 shows that the time from implantation to significant release of active agent (lag time) increases with decreasing amounts of hydrophilic end PLGA in the ocular implant. In FIG. 9, the lag time for implants having 0% hydrophilic end PLGA (40% w/w hydrophobic end) was shown to be about 21 days. In comparison, a significant reduction in lag time was seen with implants having 10% w/w and 20% w/w hydrophilic end PLGA.

Release Kinetics

The inventors believe the implants of the invention are formulated with particles of an active agent dispersed within a biodegradable polymer matrix. Without being bound by theory, the inventors believe that release of the active agent is achieved by erosion of the biodegradable polymer matrix and by diffusion of the particulate agent into an ocular fluid, e.g., the vitreous, with subsequent dissolution of the polymer matrix and release of the active agent. The inventors believe that the factors that influence the release kinetics include such characteristics as the size of the active agent particles, the solubility of the active agent, the ratio of active agent to polymer(s), the method of manufacture, the surface area exposed, and the erosion rate of the polymer(s). The release kinetics achieved by this form of active agent release are different than that achieved through formulations which release active agents through polymer swelling, such as with crosslinked hydrogels. In that case, the active agent is not released through polymer erosion, but through polymer swelling, which releases agent as liquid diffuses through the pathways exposed.

The inventors believe that the release rate of the active agent depends at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release.

The release kinetics of the implants of the invention are dependent in part on the surface area of the implants. A larger surface area exposes more polymer and active agent to ocular fluid, causing faster erosion of the polymer matrix and dissolution of the active agent particles in the fluid. The size and shape of the implant may also be used to control the rate of release, period of treatment, and active agent concentration at the site of implantation. At equal active agent loads, larger implants will deliver a proportionately larger dose, but depending on the surface to mass ratio, may possess a slower release rate. For implantation in an ocular region, the total weight of the implant preferably ranges, e.g., from about 100-5000 µg, usually from about 500-1500 µg. In one variation, the total weight of the implant is about 600 µg. In another variation, the total weight of the implant is about 1200 µg.

The bioerodible implants are typically solid, and may be formed as particles, sheets, patches, plaques, films, discs, fibers, rods, and the like, or may be of any size or shape compatible with the selected site of implantation, as long as the implants have the desired release kinetics and deliver an amount of active agent that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In one variation, the rods have diameters of about 0.1 mm to about 1 mm. In another variation, the rods have diameters of about 0.3 mm to about 0.75 mm. In yet a further variation, other implants having variable geometries but approximately similar volumes may also be used.

As previously discussed, the release of an active agent from a biodegradable polymer matrix may also be modulated by varying the ratio of hydrophilic end PLGA to hydrophobic end PLGA in the matrix. Release rates may be further manipulated by the method used to manufacture the implant. For instance, as illustrated in Examples 4-7, extruded 60/40 w/w dexamethasone/PLGA implants having a ratio of hydrophilic end and hydrophobic end PLGA of 3:1, compared to compressed tablet implants, demonstrate a different drug release profile and concentration of agent in the vitreous over about a one month period. Overall, a lower burst of agent release and a more consistent level of agent in the vitreous is demonstrated with the extruded implants.

Figure 2:
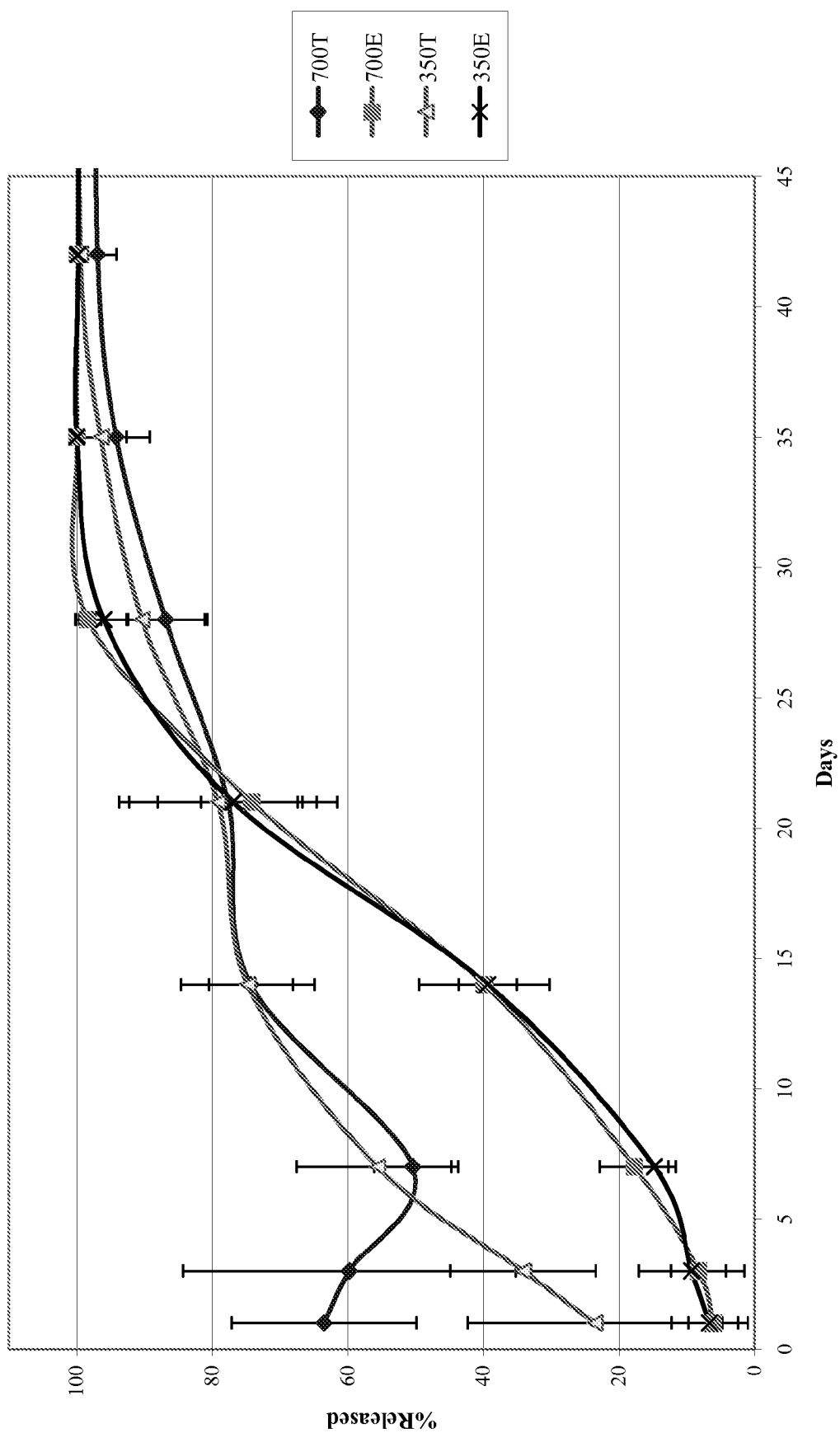
FIG. 2 shows the in vivo cumulative percentage release of dexamethasone in the vitreous of rabbit eyes over a 42 day period after implantation of compressed and extruded biodegradable implants containing 350 μg dexamethasone and 700 μg dexamethasone into the posterior segment of rabbit eyes.

As shown in FIG. 2 and Examples 4 and 5, a higher initial burst of active agent release occurs on day one after implantation with the 350 µg dexamethasone compressed tablet implant (350T) in comparison to the 350 µg dexamethasone extruded implant (350E). A higher initial burst of active agent release also occurs with the 700 µg dexamethasone compressed implant (700T) in comparison to the 700 µg dexamethasone extruded implant (700E) on day 1, as shown in FIG. 2 and Examples 6 and 7.

The proportions of active agent, biodegradable polymer matrix, and any other additives may be empirically determined by formulating several implants with varying proportions and determining the release profile in vitro or in vivo. A USP approved method for dissolution or release test can be used to measure the rate of release in vitro (USP 24; NF 19 (2000) pp. 1941-1951). For example, a weighed sample of the implant is added to a measured volume of a solution containing 0.9% NaCl in water, where the solution volume will be such that the active agent concentration after release is less than 20% of saturation. The mixture is maintained at 37° C. and stirred or shaken slowly to maintain the implants in suspension. The release of the dissolved active agent as a function of time may then be followed by various methods known in the art, such as spectrophotometrically, HPLC, mass spectroscopy, and the like, until the solution concentration becomes constant or until greater than 90% of the active agent has been released.

In one variation, the extruded implants described herewith (ratio of hydrophilic end PLGA to hydrophobic end PLGA of 3:1) may have in vivo cumulative percentage release profiles with the following described characteristics, as shown in FIG. 2, where the release profiles are for release of the active agent in vivo after implantation of the implants into the vitreous of rabbit eyes. The volume of rabbit eyes is approximately 60-70% of human eyes.

At day one after implantation, the percentage in vivo cumulative release may be between about 0% and about 15%, and more usually between about 0% and about 10%. At day one after implantation, the percentage in vivo cumulative release may be less than about 15%, and more usually less than about 10%.

At day three after implantation, the percentage in vivo cumulative release may be between about 0% and about 20%, and more usually between about 5% and about 15%. At day three after implantation, the percentage in vivo cumulative release may be less than about 20%, and more usually less than about 15%.

At day seven after implantation, the percentage in vivo cumulative release may be between about 0% and about 35%, more usually between about 5% and about 30%, and more usually still between about 10% and about 25%. At day seven after implantation, the percentage in vivo cumulative release may be greater than about 2%, more usually greater than about 5%, and more usually still greater than about 10%.

At day fourteen after implantation, the percentage in vivo cumulative release may be between about 20% and about 60%, more usually between about 25% and about 55%, and more usually still between about 30% and about 50%. At day fourteen after implantation, the percentage in vivo cumulative release may be greater than about 20%, more usually greater than about 25%, and more usually still greater than about 30%.

At day twenty-one after implantation, the percentage in vivo cumulative release may be between about 55% and about 95%, more usually between about 60% and about 90%, and more usually still between about 65% and about 85%. At day twenty-one after implantation, the percentage in vivo cumulative release may be greater than about 55%, more usually greater than about 60%, and more usually still greater than about 65%.

At day twenty-eight after implantation, the percentage in vivo cumulative release may be between about 80% and about 100%, more usually between about 85% and about 100%, and more usually still between about 90% and about 100%. At day twenty-eight after implantation, the percentage in vivo cumulative release may be greater than about 80%, more usually greater than about 85%, and more usually still greater than about 90%.

At day thirty-five after implantation, the percentage in vivo cumulative release may be between about 95% and about 100%, and more usually between about 97% and about 100%. At day thirty-five after implantation, the percentage in vivo cumulative release may be greater than about 95%, and more usually greater than about 97%.

In one variation, the percentage in vivo cumulative release has the following characteristics: one day after implantation it is less than about 15%; three days after implantation it is less than about 20%; seven days after implantation it is greater than about 5%; fourteen days after implantation it is greater than about 25%; twenty-one days after implantation it is greater than about 60%; and twenty-eight days after implantation it is greater than about 80%. In another variation, the percentage in vivo cumulative release has the following characteristics: one day after implantation it is less than about 10%; three days after implantation it is less than about 15%; seven days after implantation it is greater than about 10%; fourteen days after implantation it is greater than about 30%; twenty-one days after implantation it is greater than about 65%; twenty-eight days after implantation it is greater than about 85%.

In yet another variation, the extruded implants described in this patent may have in vitro cumulative percentage release profiles in saline solution at 37° C. with the following characteristics, as further described below, and as shown in FIG. 10.

The percentage in vitro cumulative release at day one may be between about 0% and about 5%, and more usually between about 0% and about 3%. The percentage in vitro cumulative release at day one may be less than about 5%, and more usually less than about 3%.

The percentage in vitro cumulative release at day four may be between about 0% and about 7%, and more usually between about 0% and about 5%. The percentage in vitro cumulative release at day four may be less than about 7%, and more usually less than about 5%.

The percentage in vitro cumulative release at day seven may be between about 1% and about 10%, and more usually between about 2% and about 8%. The percentage in vitro cumulative release at day seven may be greater than about 1%, and more usually greater than about 2%.

The percentage in vitro cumulative release at day 14 may be between about 25% and about 65%, more usually between about 30% and about 60%, and more usually still between about 35% and about 55%. The percentage in vitro cumulative release at day 14 may be greater than about 25%, more usually greater than about 30%, and more usually still greater than about 35%.

The percentage in vitro cumulative release at day 21 may be between about 60% and about 100%, more usually between about 65% and about 95%, and more usually still between about 70% and about 90%. The percentage in vitro cumulative release at day 21 may be greater than about 60%, more usually greater than about 65%, and more usually still greater than about 70%.

The percentage in vitro cumulative release at day 28 may be between about 75% and about 100%, more usually between about 80% and about 100%, and more usually still between about 85% and about 95%. The percentage in vitro cumulative release at day 28 may be greater than about 75%, more usually greater than about 80%, and more usually still greater than about 85%.

The percentage in vitro cumulative release at day 35 may be between about 85% and about 100%, more usually between about 90% and about 100%, and more usually still between about 95% and about 100%. The percentage in vitro cumulative release at day 35 may be greater than about 85%, more usually greater than about 90%, and more usually still greater than about 95%.

In one variation, the percentage in vitro cumulative release has the following characteristics: after one day it is less than about 1%; after four days it is less than about 7%; after seven days it is greater than about 2%; after 14 days it is greater than about 30%; after 21 days it is greater than about 65%; after 28 days it is greater than about 80%; and after 35 days it is greater than about 90%. In another variation, the percentage in vitro cumulative release has the following characteristics: after one day it is less than about 3%; after four days it is less than about 5%; after seven days it is greater than about 2%; after 14 days it is greater than about 35%; after 21 days it is greater than about 70%; after 28 days it is greater than about 85%; and after 35 days it is greater than about 90%.

Besides showing a lower burst effect for the extruded implants, FIGS. 2 and 10 also demonstrate that after 28 days in vivo in rabbit eyes, or in vitro in a saline solution at 37° C., respectively, almost all of the active agent has been released from the implants. Furthermore, FIGS. 2 and 10 show that the active agent release profiles for the extruded implants in vivo (from the time of implantation) and in vitro (from the time of placement into a saline solution at 37° C.) are substantially similar and follow approximately a sigmoidal curve, releasing substantially all of the active agent over 28 days. From day one to approximately day 17, the curves show approximately an upward curvature (i.e., the derivative of the curve increases as time increases), and from approximately day 17 onwards the curves show approximately a downward curvature (i.e., the derivative of the curve decreases as time increases).

Figure 1:
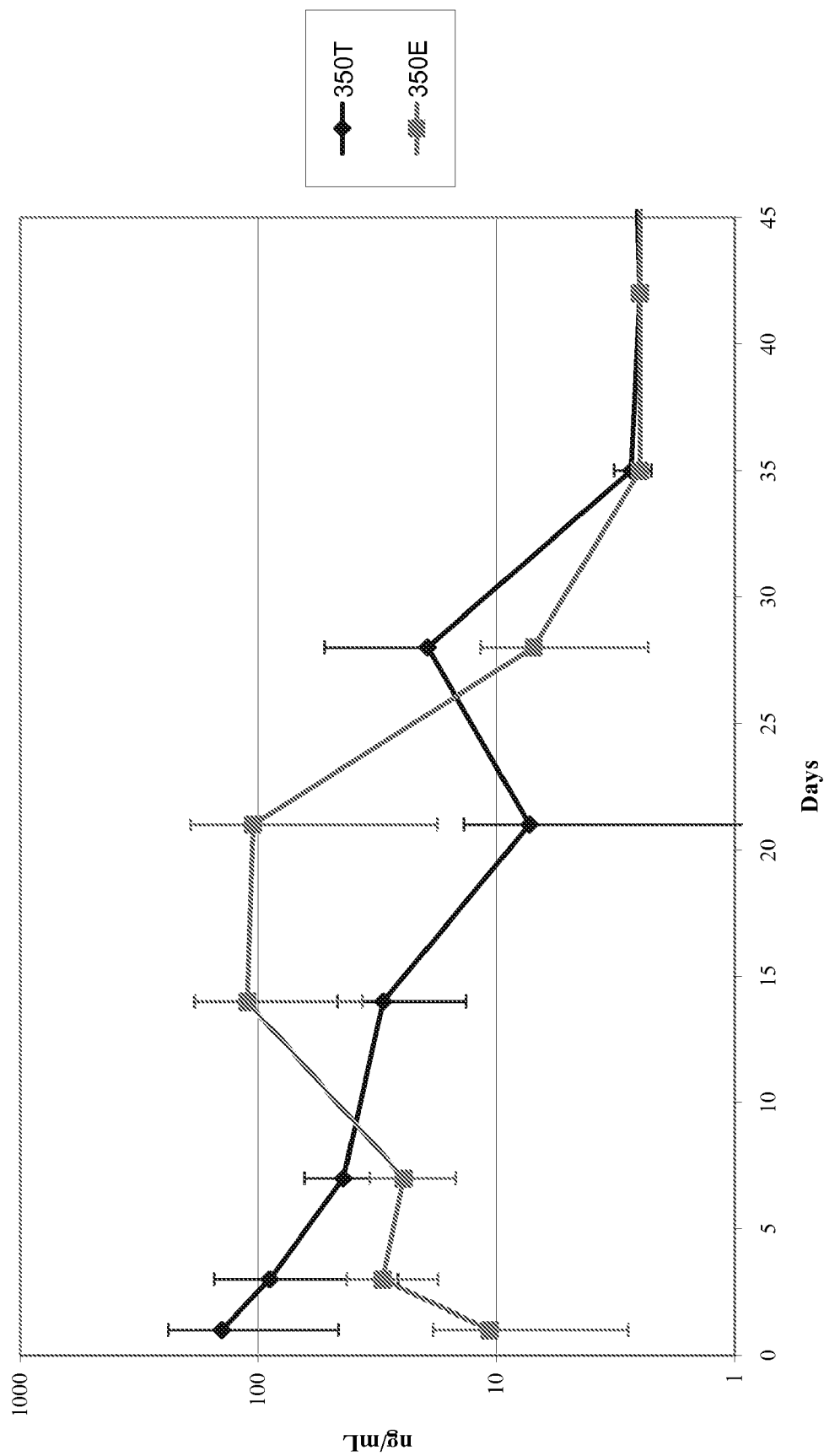
FIG. 1 shows the in vivo concentration of dexamethasone in the vitreous of rabbit eyes over a 42 day period after implantation of compressed and extruded biodegradable implants containing 350 μg dexamethasone into the posterior segment of rabbit eyes.
Figure 5:
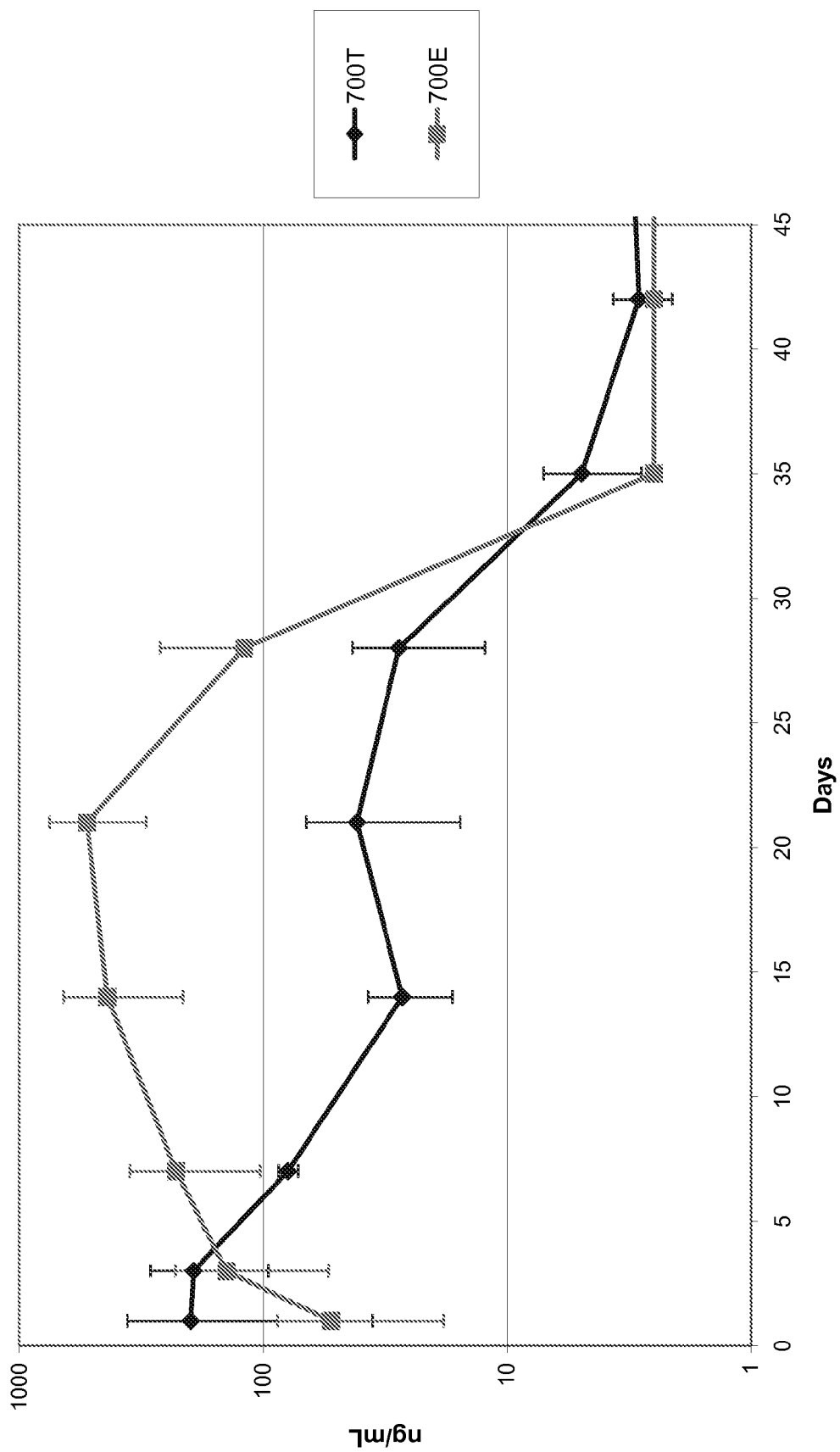
FIG. 5 shows the in vivo concentration of dexamethasone in the vitreous of rabbit eyes over a 42 day period after implantation of compressed and extruded biodegradable implants containing 700 μg dexamethasone into the posterior segment of rabbit eyes.

In contrast, the plots shown in FIG. 2 for the 350 µg and 700 µg dexamethasone compressed tablet implants exhibit a higher initial burst of agent release generally followed by a gradual increase in release. Furthermore, as shown in FIGS. 1 and 5, implantation of a compressed implant results in different concentrations of active agent in the vitreous at various time points from implants that have been extruded. For example, as shown in FIGS. 1 and 5, with extruded implants there is a gradual increase, plateau, and gradual decrease in intravitreal agent concentrations. In contrast, for compressed tablet implants, there is a higher initial active agent release followed by an approximately constant decrease over time. Consequently, the intravitreal concentration curve for extruded implants results in more sustained levels of active agent in the ocular region.

In addition to the previously described implants releasing substantially all of the therapeutic agent within 35 days, by varying implant components including, but not limited to, the composition of the biodegradable polymer matrix, implants may also be formulated to release a therapeutic agent for any desirable duration of time, for example, for about one week, for about two weeks, for about three weeks, for about four weeks, for about five weeks, for about six weeks, for about seven weeks, for about eight weeks, for about nine weeks, for about ten weeks, for about eleven weeks, for about twelve weeks, or for more than 12 weeks.

Figure 8:
FIG. 8 shows the in vivo concentration of dexamethasone in the vitreous of rabbit eyes over a 42 day period after implantation of compressed and extruded biodegradable implants containing 350 μg dexamethasone and 700 μg dexamethasone into the posterior segment of rabbit eyes.

Another important feature of the extruded implants is that different concentration levels of active agent may be established in the vitreous using different doses of the active agent. As illustrated in FIG. 8, the concentration of agent in the vitreous is significantly larger with the 700 µg dexamethasone extruded implant than with the 350 µg dexamethasone extruded implant. Different active agent concentrations are not demonstrated with the compressed tablet implant. Thus, by using an extruded implant, it is possible to more easily control the concentration of active agent in the vitreous. In particular, specific dose-response relationships may be established since the implants can be sized to deliver a predetermined amount of active agent.

Applications

Examples of medical conditions of the eye which may be treated by the implants and methods of the invention include, but are not limited to, uveitis, macular edema, macular degeneration, retinal detachment, ocular tumors, fungal or viral infections, multifocal choroiditis, diabetic retinopathy, proliferative vitreoretinopathy (PVR), sympathetic ophthalmia, Vogt Koyanagi-Harada (VKH) syndrome, histoplasmosis, uveal diffusion, and vascular occlusion. In one variation, the implants are particularly useful in treating such medical conditions as uveitis, macular edema, vascular occlusive conditions, proliferative vitreoretinopathy (PVR), and various other retinopathies.

Method of Implantation

The biodegradable implants may be inserted into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger.

The method of implantation generally first involves accessing the target area within the ocular region with the needle. Once within the target area, e.g., the vitreous cavity, the lever on the hand held device is depressed to cause the actuator to drive the plunger forward. As the plunger moves forward, it pushes the implant into the target area.

Extrusion Methods

The use of extrusion methods allows for large-scale manufacture of implants and results in implants with a homogeneous dispersion of the drug within the polymer matrix. When using extrusion methods, the polymers and active agents that are chosen are stable at temperatures required for manufacturing, usually at least about 50° C. Extrusion methods use temperatures of about 25° C. to about 150° C., more preferably about 60° C. to about 130° C.

Different extrusion methods may yield implants with different characteristics, including but not limited to the homogeneity of the dispersion of the active agent within the polymer matrix. For example, using a piston extruder, a single screw extruder, and a twin screw extruder will generally produce implants with progressively more homogeneous dispersion of the active. When using one extrusion method, extrusion parameters such as temperature, extrusion speed, die geometry, and die surface finish will have an effect on the release profile of the implants produced.

In one variation of producing implants by extrusion methods, the drug and polymer are first mixed at room temperature and then heated to a temperature range of about 60° C. to about 150° C., more usually to about 130° C. for a time period of about 0 to about 1 hour, more usually from about 0 to about 30 minutes, more usually still from about 5 minutes to about 15 minutes, and most usually for about 10 minutes. The implants are then extruded at a temperature of between about 60° C. to about 130° C., preferably at a temperature of between about 75° C. and 110° C., and more preferably at a temperature of about 90° C.

In a preferred extrusion method, the powder blend of active agent and PLGA is added to a single or twin screw extruder preset at a temperature of about 80° C. to about 130° C., and directly extruded as a filament or rod with minimal residence time in the extruder. The extruded filament or rod is then cut into small implants having the loading dose of active agent appropriate to treat the medical condition of its intended use.

DEX PS DDS

The present invention is based upon the discovery of an intraocular drug delivery system which can address many of the problems associated with conventional therapies for the treatment of ocular conditions, such as posterior segment inflammation, including fluctuating drug levels, short intraocular half-life, and prolonged systemic exposure to high levels of corticosteroids. The intraocular drug delivery system of the present invention encompasses use of dexamethasone as the active pharmaceutical agent, in which case the intraocular drug delivery system of the present invention can be referred to as a Dexamethasone Posterior Segment Drug Delivery System (DEX PS DDS). The DEX PS DDS is intended for placement into the posterior segment by a pars plana injection, a familiar method of administration for ophthalmologists. The DEX PS DDS can be comprised of a biodegradable copolymer, poly(lactic glycolic) acid (PLGA), containing micronised dexamethasone. The DEX PS DDS can release dexamethasone, providing a total dose of approximately 350 or 700 µg over approximately 35 days. In comparison, other routes of administration (topical, periocular, systemic and standard intravitreal injections) require much higher daily doses to deliver equivalent levels of dexamethasone to the posterior segment while also exposing non-target organs to corticosteroids. Topical administration of 2 drops of dexamethasone ophthalmic suspension 0.1% four times daily to both eyes is equivalent to almost 500 µg per day. Systemic doses may be as high as 1,000 µg/kg/day (Pinar V. Intermediate uveitis. Massachusetts Eye & Ear Infirmary Immunology Service. http://www.immunology.meei.harvard.edu/im-ed.htm. 1998; Weisbecker C A, Fraunfelder F T, Naidoff M, Tippermann R, eds. 1999 Physicians' Desk Reference for Ophthalmology, 27th ed. Montvale, N.J.: Medical Economics Company, 1998; 7-8, 278-279). With the DEX PS DDS, substantially lower daily doses of dexamethasone can be administered directly to the posterior segment compared to the doses needed with conventional topical, systemic, or intravitreal therapies, thereby minimizing potential side effects. While releasing dexamethasone, the polymer can gradually degrades completely over time so there is no need to remove the DEX PS DDS after it's placement into the posterior segment of a patient eye.

To facilitate delivery of DEX PS DDS into the posterior segment of the eye, an applicator has been designed to deliver the DEX PS DDS directly into the vitreous. The DDS Applicator allows placement of the DEX PS DDS into the posterior segment through a small hollow gauge needle, thereby decreasing the morbidity associated with surgery and pars plana injection at vitrectomy. The extruded DEX PS DDS is placed in the Applicator during the manufacturing of the sterile finished drug product. The DEX PS DDS Applicator System can be a single-use only device.

700 µg and 350 µg Dexamethasone Posterior Segment Drug Delivery System (DEX PS DDS Applicator System) can be used in the treatment of, for example, patients with macular oedema following central retinal vein occlusion or branch retinal vein occlusion.

Dexamethasone can be obtained from Aventis Pharma, Montvale, N.J., U.S.A. The chemical name of dexamethasone is pregna-1,4-diene-3,20-dione-9-fluoro-11,17,21-trihydroxy-16-methyl-, (11β,16α), and it's chemical structure can be represented diagrammatically as follows:

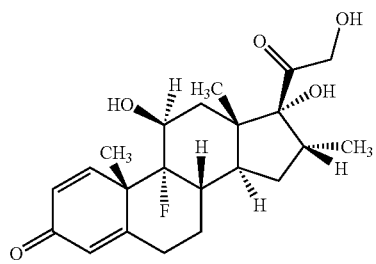

Other characteristics of dexamethasone are:

| Molecular Formula: | $C_{22}H_{29}FO_5$ |
| --- | --- |
| Molecular Weight: | 392.47 |
| Chirality/Stereochemistry: | Dexamethasone has 8 chiral centres and is optically active |
| Description: | White or almost white, crystalline powder |
| pH and pKa: | Dexamethasone has no ionisable groups |
| Melting Point: | 253° C. to 255° C. |
| Solubility: | Water: practically insoluble |
| | Ethanol: Sparingly soluble |
| | Methylene chloride: slightly soluble |

Further information on the physical and chemical properties of dexamethasone is summarised in the current European Pharmacopoeia (Ph. Eur.).

An embodiment of our invention can be referred to as a DEX PS DDS. DEX PS DDS is an implant (a drug delivery system or DDS) for intravitreal (i.e. posterior segment, or PS) use, comprised of dexamethasone (i.e. DEX) (drug substance) and a polymer matrix of 50:50 poly(D,L-lactide-co-glycolide) PLGA, constituted of two grades of PLGA (50:50 PLGA ester and 50:50 PLGA acid). See Table 1 for details. This biodegradable drug delivery system is designed to release the drug substance into the posterior segment of the eye over a 35-day period. DEX PS DDS can be implanted into the vitreous humour of the eye using an applicator system.

Two dose levels, one containing 350 µg and one containing 700 µg of dexamethasone, have been evaluated in a clinical trial. Both dose levels have the same formulation as detailed in Table 2. They are prepared using the same bulk and double extrusion process, but cut to different lengths to obtain the appropriate dosage strength.

TABLE 1

Qualitative composition of a sample DEX PS DDS

| Component | Quality Standard | Function |
| --- | --- | --- |
| Dexamethasone | Ph. Eur. | Active ingredient |
| 50:50 PLGA ester | Allergan, Inc. | Biodegradable extended release polymer matrix |
| 50:50 PLGA acid | Allergan, Inc. | Biodegradable extended release polymer matrix |

TABLE 2

Quantitative Composition of a sample DEX PS DDS (manufacturing batch formula)

| | 350 µg | 700 µg | |
| --- | --- | --- | --- |
| | Formula number | | Representative 80 g |
| Component | 9635X | 9632X | Batch Quantity |
| Dexamethasone | 350 µg (60%) | 700 µg (60%) | 48 grams |
| 50:50 PLGA ester (hydrophobic) | 58 µg (10%) | 116 µg (10%) | 8 grams |
| 50:50 PLGA acid (hydrophilic) | 175 µg (30%) | 350 µg (30%) | 24 grams |

The drug substance used in the DEX PS DDS is dexamethasone micronised.

DEX PS DDS can contain two excipients (i.e. non-active ingredients) which can be present as two different grades of the same biodegradable polymer 50:50 Poly (D,L lactide-co-glycolide) (PLGA), which can be supplied by Boehringer Ingelheim: 50:50 PLGA ester and 50:50 PLGA acid.

Poly D,L lactide-co-glycolide has been used for more than 15 years in parenteral products and is a main component of absorbable sutures. A list of some of the medical products commercially available is supplied in Table 3.

chosen is 50:50 PLGA. The rate of release is mainly linked to the rate of degradation of the PLGA, depending on several factors such as molecular weight and weight distribution, lactide to glycolide ratio, polymeric chain endings, etc. The

TABLE 3

List of commercial medical products containing PLGA

| Name | Manufacturer | Drug Substance | Dosage form | Mode of administration |
|---|---|---|---|---|
| Vicryl ® | Ethicon | Suture used in ocular surgery | | |
| Enantone ® | Takeda | Leuprorelin | Microsphere suspension | Injection (SC or IM) |
| Prostap ® | Wyeth | Leuprorelin acetate | Microsphere suspension | Injection (SC or IM) |
| Bigonist ® | Aventis | Buserelin | Implant | Injection (SC) |
| Somatuline ® | Beaufour Ipsen Pharma | Lanreotide acetate | Microparticle suspension | Injection (IM) |
| Sandostatin ® | Novartis | Octreotide acetate | Microsphere suspension | Injection (IM) |
| Zoladex ® | Astra Zeneca | Goserelin acetate | Implant | Injection (SC) |
| Risperdal consta ® | Janssen-Cilag | Risperidone | Microparticle suspension | Injection (IM) |
| Decapeptyl ® | Ipsen | Triptorelin | | Injection (IM) |
| Gonapeptyl Depot ® | Ferring Pharmaceutical | Triptorelin | Microparticle suspension | Injection (SC or IM) |

PLGA exists in different grades depending on the ratio of lactide to glycolide and polymer chain ending. All PLGAs degrade via backbone hydrolysis (bulk erosion), and the degradation products, lactic acid and glycolic acid, are ultimately metabolised by the body into $CO_2$ and $H_2O$. The two PLGAs combination as presented in Table 2 was chosen in order to obtain a drug substance release over a 35-day period. General properties of the chosen PLGAs are presented in Table 4.

mechanism for the degradation of PLGA is a hydrolysis triggered by the presence of body fluids i.e. vitreous humour in the case of DEX PS DDS.

Early formulations contained only one grade of PLGA (50/50 ratio with ester end) custom synthesised. Subsequently, it was discovered that the "acid end" form of PLGA designated 50:50 PLGA acid, combined with the 50:50 PLGA ester (equivalent to the initial PLGA), produced the

TABLE 4

General properties of PLGAs

| | 50:50 PLGA ester | 50:50 PLGA acid |
|---|---|---|
| Common Names | Resomer RG 502, PLG, PLGA, Poly (lactic-glycolic) acid, 50:50 Poly (D,L-lactide-co-glycolide), Polylactic/Polyglycolic acid, Polyglactin 910 | Resomer RG 502H, PLG acid end, PLGA acid end, 50:50 Poly (D,L-lactide-co-glycolide) acid end |
| Structure | (structure with $CH_3$ group, $n$ and $m$ repeating units) | (structure with $CH_3$ group, $n$ and $m$ repeating units, terminal OH) |
| | Where: $n = m$ $n$ = number of lactide repeating units $m$ = number of glycolide repeating units $z$ = overall number of lactide-co-glycolide repeating units | Where: $n = m$ $n$ = number of lactide repeating units $m$ = number of glycolide repeating units $z$ = overall number of lactide-co-glycolide repeating units |
| CAS Number | 34346-01-5 | 26780-50-7 |
| Empirical Formula | [(C3H4O2)x•(C2H2O2)y]CH3, x:y = 50:50 | [(C3H4O2)x•(C2H2O2)y]OH, x:y = 50:50 |
| Description | white to off white powder | white to near white powder |

DEX PS DDS was designed to release dexamethasone in the posterior segment of the eye over an extended period of 35 days. This extended release is achieved by including dexamethasone in a biodegradable polymer matrix. The polymer desired drug release profile. "Acid end" PLGA is slightly more hydrophilic and therefore degrades faster in water. Both polymer backbones are identical, but the polymerisation process used to produce acid end PLGA involves a different chain termination agent leading to carboxylic moieties at the end of the polymer chains. During biodegradation of the implant, the degradation products are the same for both polymers, i.e. lactic acid and glycolic acid. Details of the formulation proposed can be found above. In addition, the stability of DEX PS DDS was evaluated.

EXAMPLES

The following examples serve to more fully describe the manner of using the above-described invention. It is understood that these examples in no way serve to limit the scope of this invention, but rather are presented for illustrative purposes.

Example 1

Manufacture of Compressed Tablet Implants

Micronized dexamethasone (Pharmacia, Peapack, N.J.) and micronized hydrophobic end 50/50 PLGA (Birmingham Polymers, Inc., Birmingham, Ala.) were accurately weighed and placed in a stainless steel mixing vessel. The vessel was sealed, placed on a Turbula mixer and mixed at a prescribed intensity, e.g., 96 rpm, and time, e.g., 15 minutes. The resulting powder blend was loaded one unit dose at a time into a single-cavity tablet press. The press was activated at a pre-set pressure, e.g., 25 psi, and duration, e.g., 6 seconds, and the tablet was formed and ejected from the press at room temperature. The ratio of dexamethasone to PLGA was 70/30 w/w for all compressed tablet implants.

Example 2

Manufacture of Extruded Implants

Micronized dexamethasone (Pharmacia, Peapack, N.J.) and unmicronized PLGA were accurately weighed and placed in a stainless steel mixing vessel. The vessel was sealed, placed on a Turbula mixer and mixed at a prescribed intensity, e.g., 96 rpm, and time, e.g., 10-15 minutes. The unmicronized PLGA composition comprised a 30/10 w/w mixture of hydrophilic end PLGA (Boehringer Ingelheim, Wallingford, Conn.) and hydrophobic end PLGA (Boehringer Ingelheim, Wallingford, Conn.). The resulting powder blend was fed into a DACA Microcompounder-Extruder (DACA, Goleta, Calif.) and subjected to a pre-set temperature, e.g., 115° C., and screw speed, e.g., 12 rpm. The filament was extruded into a guide mechanism and cut into exact lengths that corresponded to the designated implant weight. The ratio of dexamethasone to total PLGA (hydrophilic and hydrophobic end) was 60/40 w/w for all extruded implants.

Example 3

Method for Placing Implants into the Vitreous

Implants were placed into the posterior segment of the right eye of New Zealand White Rabbits by incising the conjunctiva and sclera between the 10 and 12 o'clock positions with a 20-gauge microvitreoretinal (MVR) blade. Fifty to 100 μL of vitreous humor was removed with a 1-cc syringe fitted with a 27-gauge needle. A sterile trocar, preloaded with the appropriate implant (drug delivery system, DDS), was inserted 5 mm through the sclerotomy, and then retracted with the push wire in place, leaving the implant in the posterior segment. Sclerae and conjunctivae were than closed using a 7-0 Vicryl suture.

Example 4

In Vivo Release of Dexamethasone from 350 μg Dexamethasone Compressed Tablet Implants Example 4 demonstrates the high initial release but generally lower intravitreal concentration of dexamethasone from compressed tablet implants as compared to extruded implants. The 350 μg compressed tablet implant (350T) was placed in the right eye of New Zealand White Rabbits as described in Example 3. Vitreous samples were taken periodically and assayed by LC/MS/MS to determine in vivo dexamethasone delivery performance. As seen in FIG. 1, dexamethasone reached detectable mean intravitreal concentrations from day 1 (142.20 ng/ml) through day 35 (2.72 ng/ml), and the intravitreal concentration of dexamethasone gradually decreased over time.

Figure 3:
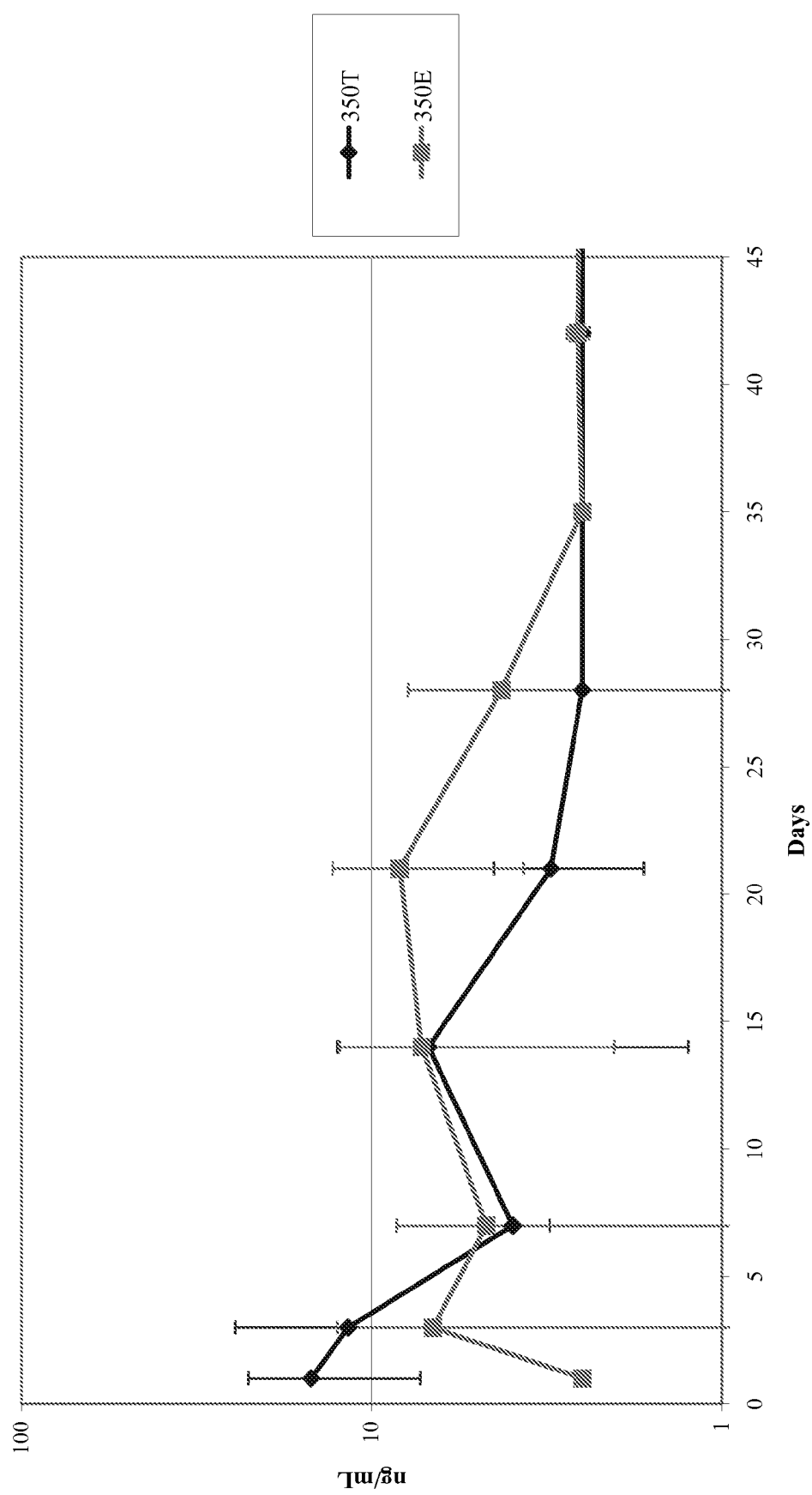
FIG. 3 shows the in vivo concentration of dexamethasone in the aqueous humor of rabbit eyes over a 42 day period after implantation of compressed and extruded biodegradable implants containing 350 μg dexamethasone into the posterior segment of rabbit eyes.
Figure 4:
FIG. 4 shows the in vivo concentration of dexamethasone in the plasma (from a rabbit blood sample) over a 42 day period after implantation of compressed and extruded biodegradable implants containing 350 μg dexamethasone into the posterior segment of rabbit eyes.

In addition to the vitreous samples, aqueous humor and plasma samples were also taken. The 350T showed a gradual decrease in aqueous humor dexamethasone concentrations over time, exhibiting a detectable mean dexamethasone aqueous humor concentration at day 1 (14.88 ng/ml) through day 21 (3.07 ng/ml), as demonstrated in FIG. 3. The levels of dexamethasone in the aqueous humor strongly correlated with the levels of dexamethasone in the vitreous humor, but at a much lower level (approximately 10-fold lower). FIG. 4 shows that only trace amounts of dexamethasone was found in the plasma.

Example 5

In Vivo Release of Dexamethasone from 350 μg Dexamethasone Extruded Implants

Example 5 demonstrates the lower initial release and generally more sustained intravitreal concentration of dexamethasone from extruded implants. The 350 μg extruded implant (350E) was placed in the right eye of New Zealand White Rabbits as described in Example 3. Vitreous samples were taken periodically and assayed by LC/MS/MS to determine in vivo dexamethasone delivery performance. Referring to FIG. 1, 350E showed detectable mean vitreous humor concentrations on day 1 (10.66 ng/ml) through day 28 (6.99 ng/ml). The 350T implant had statistically significant higher dexamethasone concentrations on day 1 (p=0.037) while the 350E had a statistically significant higher dexamethasone level on day 21 (p=0.041).

In addition to the vitreous samples, aqueous humor and plasma samples were also taken. In FIG. 3, the 350E showed detectable mean dexamethasone aqueous humor concentrations at day 1 (6.67 ng/ml) through day 42 (2.58 ng/ml) with the exception of day 35 in which the values were below the quantification limit. On the whole, the levels of dexamethasone in the aqueous strongly correlated with the levels of dexamethasone in the vitreous humor, but at a much lower level (approximately 10-fold lower). FIG. 4 demonstrates that only a trace amount of dexamethasone was found in the plasma.

Example 6

In Vivo Release of Dexamethasone from 700 μg Dexamethasone Compressed Tablet Implants Example 6 also shows the high initial release and generally lower intravitreal concentration of dexamethasone from compressed tablet implants. The 700 μg compressed tablet dosage form (700T) was placed in the right eye of New Zealand White Rabbits as described in Example 3. Vitreous samples were taken periodically and assayed by LC/MS/MS to determine in vivo dexamethasone delivery performance. As seen in FIG. 5, the 700T reached detectable mean dexamethasone vitreous humor concentrations at day 1 (198.56 ng/ml) through day 42 (2.89 ng/ml), and a gradual decrease in the intravitreal dexamethasone concentration over time.

Figure 6:
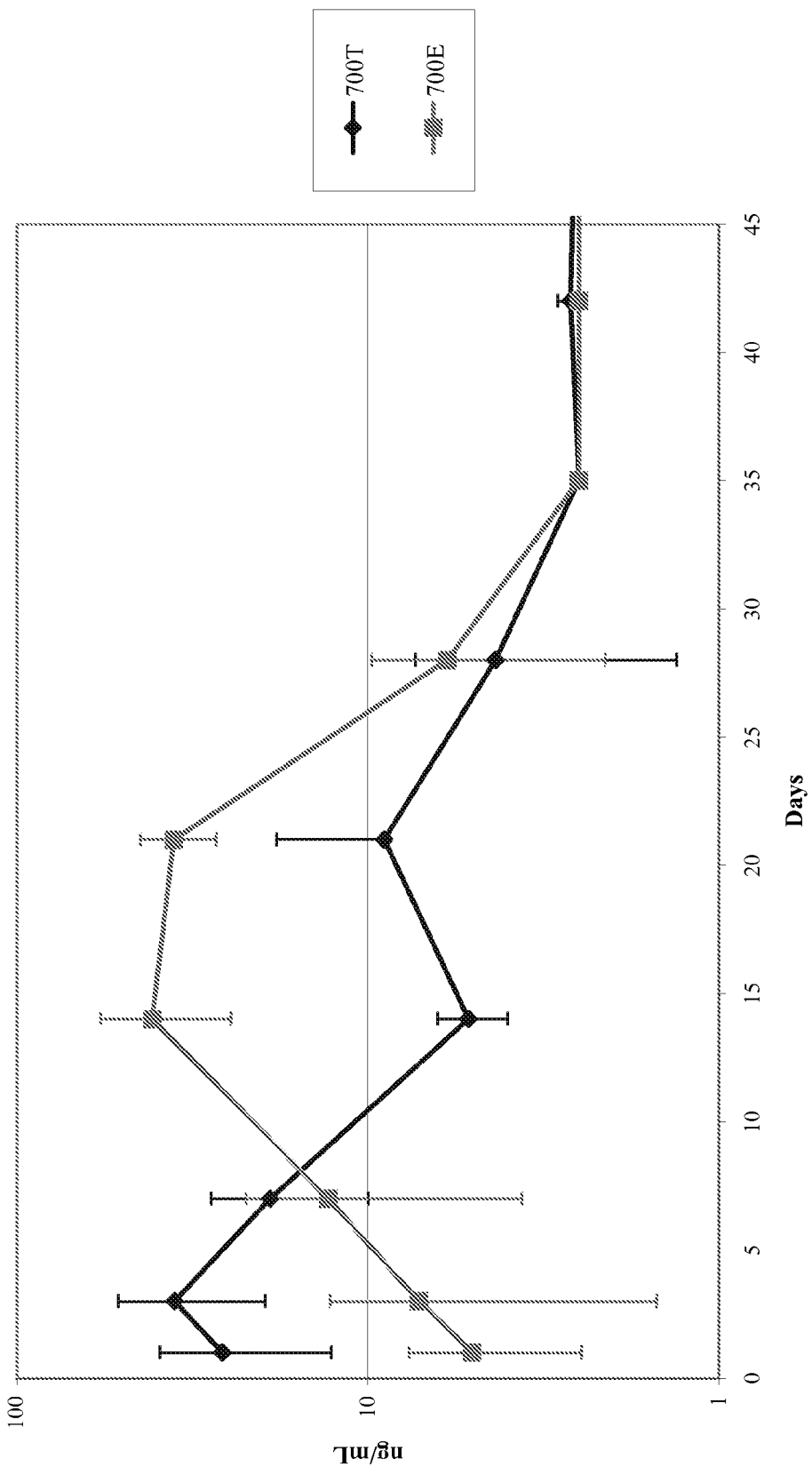
FIG. 6 shows the in vivo concentration of dexamethasone in the aqueous humor of rabbit eyes over a 42 day period after implantation of compressed and extruded biodegradable implants containing 700 μg dexamethasone into the posterior segment of rabbit eyes.
Figure 7:
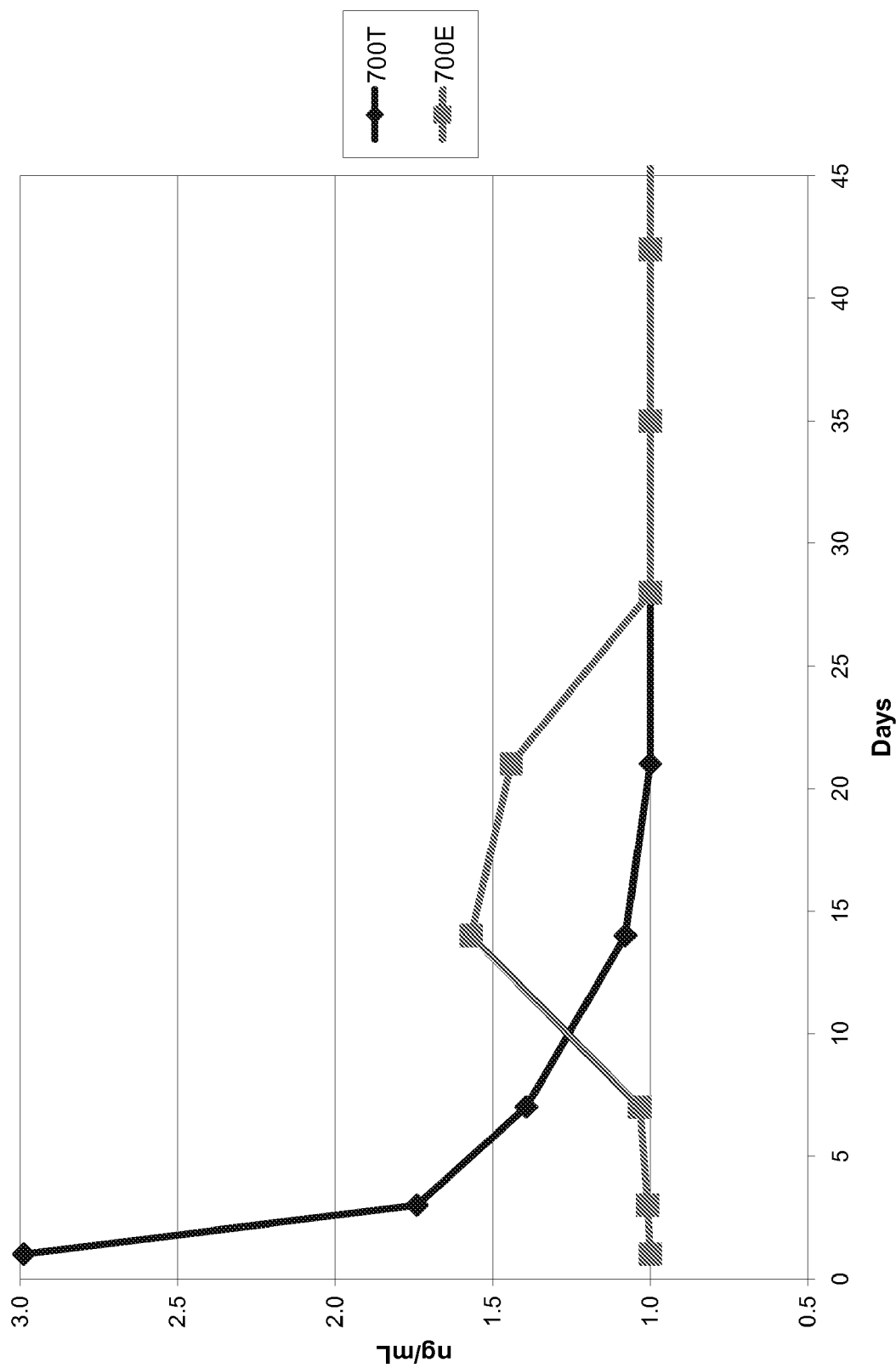
FIG. 7 shows the in vivo concentration of dexamethasone in the plasma (from a rabbit blood sample) over a 42 day period after implantation of compressed and extruded biodegradable implants containing 700 μg dexamethasone into the posterior segment of rabbit eyes.

In addition to the vitreous samples, aqueous humor and plasma samples were also obtained. As seen in FIG. 6, the 700T exhibited a gradual decrease in aqueous humor dexamethasone concentrations over time, and reached detectable mean dexamethasone aqueous humor concentrations at day 1 (25.90 ng/ml) through day 42 (2.64 ng/ml) with the exception of day 35 in which the values were below the quantification limit. The levels of dexamethasone in the aqueous humor strongly correlated with the levels of dexamethasone in the vitreous humor, but at a much lower level (approximately 10-fold lower). FIG. 7 demonstrates that only a trace amount of dexamethasone was found in the plasma.

Example 7

In Vivo Release of Dexamethasone from 700 μg Dexamethasone Extruded Implants

Example 7 also illustrates the lower initial release and generally higher intravitreal concentration of dexamethasone from extruded implants. The 700 μg extruded implant (700E) was placed in the right eye of New Zealand White Rabbits as described in Example 3. Vitreous samples were taken periodically and assayed by LC/MS/MS to determine in vivo dexamethasone delivery performance. As seen in FIG. 5, the 700E had a mean detectable vitreous humor concentration of dexamethasone from day 1 (52.63 ng/ml) through day 28 (119.70 ng/ml).

In addition to the vitreous samples, aqueous humor and plasma samples were also taken. As seen in FIG. 6, the 700E reached a detectable mean aqueous humor concentration on day 1 (5.04 ng/ml) through day 28 (5.93 ng/ml). The levels of dexamethasone in the aqueous strongly correlated with the levels of dexamethasone in the vitreous humor, but at a much lower level (approximately 10-fold lower). FIG. 7 demonstrates that only a trace amount of dexamethasone was found in the plasma.

Example 8

Extrusion Methods for Making an Implant

1. DEX PS DDS implants were made by a tabletting process, by a single extrusion process and by a double extrusion process.

The excipients (polymers) used for the DEX PS DDS implant made were two grades of 50:50 Poly(D,L lactide co glycolide) ester end and acid end. Both excipients were a pharmaceutical grade of non-compendial material.

The preferred specifications of three batches of both 50:50 Poly PLGA ester used to make implants are shown in Table A. The preferred specifications of three batches of 50:50 Poly PLGA acid use to make implants are shown in Table B.

TABLE A

Preferred Specifications for 50:50 PLGA ester

| Tests | Specifications | 1001933 | 1004907 | 1004925 |
|---|---|---|---|---|
| Appearance: Colour and shape | White to off white | Off white | Off white | Off white |
| Odour | Odourless to almost odourless | almost odourless | almost odourless | almost odourless |
| Identification | $^1H$-NMR spectra conforms to reference | conforms | conforms | conforms |
| Polymer composition | | | | |
| DL-Lactide units | 48 to 52% | 51 | 51 | 51 |
| Glycolide units | 52 to 48% | 49 | 49 | 49 |
| Inherent viscosity | 0.16 to 0.24 dl/g | 0.24 | 0.19 | 0.19 |
| Water | ≦0.5% | Conforms | Conforms | Conforms |
| Residual monomers | | | | |
| DL-lactide | ≦0.5% | Conforms | Conforms | Conforms |
| Glycolide | ≦0.5% | Conforms | Conforms | Conforms |
| Residual solvents | | | | |
| Acetone | ≦0.1% | Conforms | Conforms | Conforms |
| Toluene | ≦0.089% | Conforms | Conforms | Conforms |
| Total | ≦0.1% | Conforms | Conforms | Conforms |
| Tin | ≦100 ppm | 30 | 31 | 35 |
| Heavy metals | ≦10 ppm | Conforms | Conforms | Conforms |
| Sulphated ashes | ≦0.1% | Conforms | Conforms | Conforms |

TABLE B

Preferred Specifications for 50:50 PLGA acid

| Test | Specification | 1006825 | 1008386 | 1009848 |
|---|---|---|---|---|
| Appearance: Colour and shape | White to nearly white | White | White | Off white |
| Odour | Odourless to nearly odourless | Odourless | Odourless | Almost odourless |
| Identification | $^1H$-NMR spectra conforms to reference | Conforms | Conforms | Conforms |
| Polymer composition | | | | |
| DL-Lactide units | 48 to 52% | 51 | 51 | 51 |
| Glycolide units | 52 to 48% | 49 | 49 | 49 |
| Inherent viscosity | 0.16 to 0.24 dl/g | 0.19 | 0.19 | 0.19 |
| Water | ≦0.5% | Conforms | Conforms | Conforms |
| Residual monomers | | | | |
| DL-lactide | ≦0.5% | Conforms | Conforms | Conforms |
| Glycolide | ≦0.5% | Conforms | Conforms | Conforms |
| Residual solvents | | | | |
| Acetone | ≦0.1% | Conforms | Conforms | Conforms |
| Toluene | ≦0.089% | Conforms | Conforms | Conforms |
| Tin | ≦200 ppm | 149 | 83 | 141 |
| Heavy metals | ≦10 ppm | Conforms | Conforms | Conforms |
| Sulphated ashes | ≦0.1% | Conforms | Conforms | Conforms |
| Acid number | ≧6.5 mgKOH/g | 11 | 9 | 12 |

Preferred Specifications of Polymers Use to Make Implants

Polymer composition: It was determined that the ratio of lactide to glycolide is essential for the kinetic of degradation of the polymer and hence the dexamethasone release profile of the implant. It was controlled in a 48% to 52% (wt %) range to ensure consistency of active agent release.

Inherent viscosity: the inherent viscosity is essential for the kinetics of degradation of the polymer and hence the dexamethasone release profile of the implant. It is a measure of the size of the polymer backbone and the size distribution (i.e. molecular weight and weight distribution). It was controlled in a 0.16 to 0.24 dl/g range to ensure consistency of release.

Water: The moisture content of the polymer influences its stability during the shelf life and is a facilitating factor for the biodegradation of the polymer matrix. It was controlled below 0.5% to ensure stability of the excipients as well as the drug substance (dexamethasone) and to ensure consistency of the (dexamethasone) release profile.

Residual monomers: residual monomers indicate the completion of the synthesis of the polymer and was controlled below 0.5 wt. %.

Residual Solvents:

Acetone was controlled to below 0.1 wt. %

Toluene was controlled to be kept below 0.0890 wt. %.

Acid number: the acid number measures the number of chain ends in the PLGA acid polymer. The number of acid polymer endings facilitates the ingress of moisture upon injection of the implant and influences the release profile of the implant. It was controlled to be higher than 6.5 mg KOH/g to ensure consistency of release profile.

Preferred Dexamethasone Characteristics

The particle size and particle size distribution of the dexamethasone is regarded as a critical parameter for the homogeneity of the DEX PS DDS. A preferred dexamethasone particle size distribution has at least 75% of the particles of dexamethasone smaller than (i.e. diameter less than) 10 μm. A more preferred dexamethasone particle size distribution has at least 99% of the particles of dexamethasone smaller than (i.e. diameter less than) 20 μm. We found that use of such small particles of dexamethasone in the implant provides for a more uniform distribution of the active agent in the implant (i.e. no clumping) which leads to a more uniform release of the active agent from the implant upon implantation of the implant.

In addition to all the Ph. Eur. tests for dexamethasone, additional tests were performed on the dexamethasone using a particle size analyser and an additional analytical method, so as to ensure that the dexamethasone used in the DEX PS DDS had the preferred or the more preferred particle size and particle size distribution.

In our invention dexamethasone a particle size and particle size distribution is an important factor because homogeneity of the dexamethasone affects release characteristics.

It is additionally preferred that the dexamethasone used in the present invention comprise ≦1% of total impurities, including ≦0.50% of dexamethasone acetate, ≦0.25% of betamethasone, ≦0.25% of 3 keto delta 4 derivative and ≦0.10% of any other impurity.

A representative formula for a typical 80 g manufacturing batch (used to make an implant manufactured by the tabletting, single extrusion or double extrusion process) is provided in Table 2. For the 350 μg and 700 μg dosages, the bulk manufacturing and terminal sterilisation processes are identical.

A flow diagram of the three different manufacturing processes is shown by FIG. 11.

2. A single extrusion process was used to made an implant. In a continuous extrusion, single extrusion manufacturing process, the micronised dexamethasone and un-micronised polymer was blended, before being loaded into a twin-screw compound extruder, and then subjected to a set temperature and screw speed. The filament was extruded into a guide mechanism and cut into exact lengths that correspond to the correct DEX PS DDS weight. This continuous extrusion process was more controllable and more predictable than the tabletting process. This is illustrated in the in vitro release profiles of the DEX PS DDS as show in FIG. 12.

Four lots of 700 μg DEX PS DDS, two manufactured by the tabletting process and two by the single extrusion process were studied. With the single extrusion process the only difference between the two doses is that the 350 μg dose filament is cut from the same extrudate (same formulation) as 700 μg dose filament but is half as long. At 5 time points, over a 28-day period, 12 DEX PS DDS units from each lot were tested. The standard deviations for the mean dexamethasone release rates were found larger for the two tabletted lots than for the two extruded lots. A three-fold reduction in standard deviations across the release profile was observed with the extruded versus the tabletted product. In addition, the initial burst release is reduced with implants manufactured by a single extrusion process, as compared to implants made by a tabletting process.

These results were confirmed in a GLP in vivo pharmacokinetics study in rabbits comparing the release of dexamethasone from the tabletted and the extruded DEX PS DDS. It was shown that the tabletted and the single extruded DEX PS DDS release the same amount of dexamethasone over the same period, providing approximately a 35-day delivery.

To further characterise and compare the DEX PS DDS manufactured by the tabletting and single extrusion processes, scanning electron microscope (SEM) photographs were taken to assess physical appearance. FIG. 13 shows that the single extruded DEX PS DDS is more uniform than was the tabletted implant. It was found that not only is this gives a more consistent in vitro release profile from the single extruded implant, but also with its increased resistance to crushing. Using a texture analyser it was shown that a 3-fold increase in force (1200 g compared to 400 g) was required to crush a single extruded implant compared to a tabletted one. This demonstrates that the extruded product is more able to withstand handling.

Additionally, it was determined that the DEX PS DDS made by single extrusion and by double extrusion processes is stable during a minimum of 12 months (and for as long as 18-24 months) when stored at 25° C./60% RH and a minimum of 6 months at 40° C./75% RH. Stability was determined based upon dexamethasone potency, dexamethasone impurities (acid, ketone, aldehyde and total impurities), moisture content, applicator actuation force, implant fracture force/fracture energy and in vitro dissolution dexamethasone release profile and sterility.

3. The inventors improved the single extrusion process by (1) micronising the polymers prior to blending and (2) adding a second extrusion after pelletisation of the first extruded filament. When both 50:50 PLGA acid and 50:50 PLGA ester were micronised an acceptable DEX PS DDS homogeneity was obtained. Homogeneity promotes a more even and regular dissolution of the polymer and release of the dexamethasone active agent. The PLGAs were milled using an air jet process. FIG. 14 presents batch-to-batch versus in-batch variability from batches made of milled (i.e. micronised) and un-milled (i.e. unmicronized) PLGAs. It clearly demonstrates that the double extrusion process allows better control, especially where in-batch variability was reduced from a 94.7% LC to 107.0% LC range (unmilled PLGAs) to a 98.9% LC to 101.5% LC range (milled PLGAs. "LC" means label claim (a regulatory term), that is the amount of dexamethasone present in the implant (350 μg or 700 μg), as measured by various in vitro assays, such as by HPLC.

Single and double extrusion processes were compared. As shown by FIG. 15 implants made by a double extrusion process had released about 60% of the dexamethasone by day 14, while the single extrusion implants had released about 40% of its dexamethasone load by day 14, although total dexamethasone released was comparable by day 21. Therefore, where more release of dexamethasone is desired sooner, the double extrusion process is a preferred process for making the DEX PS DDS. A double extrusion process also provides for a higher yield of the desired filament implant, i.e. with a uniform distribution of dexamethasone throughout the implant polymer.

A detailed manufacturing schematic flow diagram for the double extrusion implant is provided by FIG. 16. The major equipment used in the manufacture of DEX PS DDS is listed in Table C.

TABLE C

Major Equipment Used in the Manufacture of DEX PS DDS

| Step | Purpose | Equipment Description |
|---|---|---|
| 1 | Milling both PLGAs | Jet Mill |
| 2 | Powder blending | Shaker |
| 3 | First extrusion | Extruder and Force Feeder, Puller Assembly and Filament Cutter |
| 4 | Pelletising | Stainless steel ball and bottle Shaker |
| 5 | Second extrusion | Extruder and Force Feeder, Puller Assembly and Filament Cutter |
| 6 | Automated DDS cutting and inspection procedure | Guillotine Cutter and Vision Inspection System |
| 7-8 | Applicator Assembly | Applicator loading fixture and Heat sealer |

4. The specifics of the double extrusion process used are as follows (a) Milling of PLGAs (Resomers RG502 and RG502H)

30 grams of RG502 (50:50 PLGA ester) were milled using the Jet-Mill (a vibratory feeder) at milling pressures of 60 psi, 80 psi and 80 psi for the pusher nozzle, grinding nozzle, and grinding nozzle, respectively. Next, 60 grams of RG502H were milled using the Jet-Mill at milling pressure of 20 psi, 40 psi and 40 psi for the pusher nozzle, grinding nozzle, and grinding nozzle, respectively. The mean particle size of both RG502 and RG502H was measured using a TSI 3225 Aerosizer DSP Particle Size Analyzer. Preferably, both milled polymers must have a mean particle size of no greater than 20 um.

(b) Blending of PLGAs and Dexamethasone 48 grams of dexamethasone, 24 grams of milled RG502H and 8 grams of milled RG502 were blended using the Turbula Shaker set at 96 RPM for 60 minutes.

(c) First Extrusion (1) All 80 grams of the blended dexamethasone/RG502H/RG502 mixture was added to the hopper of a Haake Twin Screw Extruder. The Haake extruder was turned on and set the following parameters:

Barrel Temperature: 105 degrees C.

Nozzle Temperature: 102 degrees C.

Screw Speed: 120 RPM

Feed Rate Setting: 250

Guide Plate Temperature: 50-55 degrees C.

Circulating water bath: 10 degrees C.

(2) Filament were collected. The first filament comes out about 15-25 minutes after the addition of the powder blend. Discard the first 5 minute of extruded filaments. Collecting the remaining filaments until exhaustion of extrudates; this normally takes 3-5 hours.

(d) Pelletization

The filaments from step 3 above were pelletized using the Turbula Shaker and one 19 mm stainless steel ball set at 96 RPM for 5 minutes.

(e) Second Extrusion (1) All pellets were added into the same hopper and the Haake extruder was turned on.

The following parameters were set on the Haake extruder:

Barrel Temperature: 107 degrees C.

Nozzle temperature: 90 degrees C.

Screw speed: 100 RPM

Guide Plate Temperature: 60-65 degrees C.

Circulation water bath: 10 degrees C.

(2) All extruded filaments were collected until exhaustion of extrudates. This normally takes about 3 hours.

(f) Processing of Bulk Filament to Dosage Strengths—350 µg or 700 µg

DEX PS DDS was be prepared as 350 µg or 700 µg dosage forms by cutting the filaments to the appropriate length.

(g) Insertion of DEX PS DDS into the Applicator

The DEX PS DDS was inserted into the Applicator System during the applicator assembly process. All operations took place in a Class 10 000 clean room.

(h) Packaging of DEX PS DDS Applicator System

The assembled DEX PS DDS Applicator System was placed into a foil pouch containing a small bag of desiccant and heat-sealed. Samples for pre-sterilisation bioburden testing were taken prior to step 9.

(i) Gamma Radiation Sterilization of DEX PS DDS Applicator System

The sealed foil pouches containing the finished DEX PS DDS Applicator System and a small desiccant bag were placed into a cardboard box and the box sealed. Terminal sterilisation of these product containing boxes was accomplished by exposure to a dose within the range of 25-40 kGy of gamma-radiation. Samples from each batch were tested for sterility according to Ph. Eur. and USP requirement.

(j) Labelling of DEX PS DDS Applicator

The single and double extruded implants had the preferred characteristics shown by Tables D and E, respectively.

TABLE D

In Process Controls results for the first extrusion

| | | Batch Number | | |
|---|---|---|---|---|
| | | 03J001 | 03H004 | 03M001 |
| | | Batch size | | |
| Parameter | Specifications | 80 g | 80 g | 80 g |
| Filament density | 0.85 to 1.14 g/cm$^3$ | 1.03 | 1.01 | 1.04 |
| Uniformity | 85.0 to 115.0%[1] | 99.3 | 100.5 | 98.7 |
| Potency | 97.0 to 103.0% label strength | 100.1 | 100.0 | 99.8 |
| Degradation products | ≦1.5% total | 0.2 | 0.2 | 0.2 |
| | ≦0.75% acid | ND | ND | ND |
| | ≦0.75% ketone | ≦0.08 | ≦0.10 | ≦0.13 |
| | ≦0.75% aldehyde | ≦0.15 | ≦0.10 | ≦0.12 |

[1]Percentage of target weight

TABLE E

In Process Control results for the second extrusion

| | | Batch number | | |
|---|---|---|---|---|
| | | 03J001 | 03H004 | 03M001 |
| | | | Batch size | |
| Parameter | Specifications | 80 g | 80 g | 80 g |
| Appearance | White to off white | pass | pass | pass |
| Filament density | 1.10 to 1.30 g/cm³ | 1.18 | 1.13 | 1.19 |
| Diameter | ≧80% within 0.0175 to 0.0185 inch | 100 | 100 | 100 |
| Fracture force | ≧2 g | 9.88 | 9.39 | 9.52 |
| Fracture energy | ≧0.9 μJ | 5.88 | 4.54 | 4.64 |
| Moisture | ≦1.0% | 0.4 | 0.4 | 0.4 |
| Foreign particulate | No visible foreign materials | Pass | Pass | Pass |
| Insoluble mater (for information only) | Particle count Diameter ≦10 μm Diameter ≦25 μm | 17 0.5 | 26 1 | 2.6 0 |
| Dexamethasone identity | Positive for dexamethasone | positive | positive | positive |
| Potency | 95.0 to 105.0% label strength | 98.5 | 101.2 | 99.9 |
| Degradation products | ≦2% total ≦0.5% acid ≦1.0% ketone ≦1.0% aldehyde | 1.1 ND 0.4 0.7 | 0.6 ND 0.2 0.4 | 1.0 ND 0.4 0.5 |
| Dexamethasone release | See Table 2.1.P.5.1-1 | Pass | Pass | Pass |
| Uniformity | 85.0-115.0% Label Strength (LS) Stage 1 (n = 10): If one unit is outside the range and between 75% and 125% LS or RSD ≧ 6.0%, test 20 more units. Stage 2 (n = 20): pass if no more than 1 unit is outside the range, and is between 75% and 125% LS, and the RSD ≦ 7.8%. | 97.0% all values within range | 97.1% all values within range | 98.0% all values within range |

Table F sets forth further preferred specifications for both the DEX PS DDS implant and the applicator.

TABLE F

Preferred specifications

| Attribute | Specifications |
|---|---|
| Implant appearance | White to off-white, rod shaped Drug Delivery System (DDS), essentially free of foreign matter. |
| Fracture Force | Minimum 2.0 g |
| Energy | Minimum 0.85 μjoule |
| Moisture content | No more than 1% |
| Foreign particulates | No visible foreign material |
| Insoluble matter | Record particle count for information only (diameter ≧10 μm and ≧25 μm) |
| Dexamethasone identity | Positive for dexamethasone |
| Dexamethasone potency | 90.0 to 110.0% LC |
| Impurities | Dexamethasone acid not greater than 0.5% HPLC area Dexamethasone ketone not greater than 1.0% HPLC area Dexamethasone aldehyde not greater than 1.0% HPLC area Total degradation not greater than 2% HPLC area |
| Weight Range | 700 μg dose: 1.050 mg to 1.284 mg (1.167 mg +/− 10%) 350 μg dose: 0.525 mg to 0.642 mg (0.583 mg +/− 10%) |
| Content uniformity | 85% to 115% Label Claim |
| In vitro Dissolution test (% of total amount of dexamethasone released) | Ranges: 24 hours: not greater than 10.0% 7 days: not greater than 30.0% 14 days: 25.0% to 85.0% 21 days: not less than 50% |
| Applicator Actuation force required | No more than 5.0 lbs |

Implants and Applicators made as set forth above were found to be within the parameters of the preferred specifications.

Preferred Applicator A preferred applicator to use to implant the DEX PS DDS is shown in international patent publication WO 2004/026106, published Apr. 1, 2004. The applicator was designed to facilitate the insertion of the implant in the posterior segment of the eye. The implant is housed in the needle of the applicator. The applicator is designed to fit comfortably into the hand of the physician, and to allow for single-handed operation. It is similar in size to retinal forceps, measuring 165 mm in length by 13 mm in width. FIG. 17 provides a cut-away side view of the applicator illustrating the typical functions and positions of all the elements.

As the lever is depressed, it applies a force on the linkage, which collapses and moves the plunger forward into the needle, pushing the DEX PS DDS into the posterior chamber of the eye. Once the DEX PS DDS is delivered, the lever then latches within the Applicator housing to signal use and prevent any reuse. The needle used is a 22-gauge thin-wall hypodermic needle. A silicone o-ring, is placed into a slot in the needle to retain the DEX PS DDS within the needle and remains outside the eye, in contact with the conjunctiva. To ensure that air is not introduced into the eye, the applicator has been designed to vent. A small gap between the DEX PS DDS and inner needle wall allows air to move back through and out of the needle as the DEX PS DDS is being delivered. The small size of this gap prevents fluid from flowing out of the eye through the needle. The components of the Applicator that may contact the patient during use are the plunger, needle and o-ring. The plunger and needle are manufactured from materials of known biocompatibility, and with a history of human use. Biocompatibility of the o-ring was evaluated through cytotoxicity testing.

The applicator is packed with desiccant in a pouch designed to protect the implant from humidity. The packaged implant in the applicator is then sterilised by gamma irradiation. The pouch also ensures that the product remains sterile during the shelf life.

The DEX PS DDS is terminally sterilised by gamma irradiation, in its applicator as presented packed in the foil pouch, using a 25 to 40 kGy dose. Terminal sterilisation process steam sterilisation (autoclaving) is not used because the polymers used for the controlled release are extremely sensitive to moisture and heat and degrade even with non-compendial low temperature sterilisation cycles.

The DEX PS DDS Applicator System is a sterile, single use applicator intended to deliver one DEX PS DDS. The DEX PS DDS is loaded into the needle of the Applicator during the assembly process. It is then packaged in a foil pouch with desiccant and terminally sterilised by gamma irradiation.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

We claim:

1. A bioerodible implant for treating a medical condition of the eye comprising a double extruded filament including a corticosteroid uniformly dispersed within a biodegradable polymer matrix, wherein the bioerodible implant exhibits a cumulative release profile in which greater than about 80 percent of the active agent is released about 28 days after implantation of the bioerodible implant, and wherein the cumulative release profile is approximately sigmoidal in shape over about 28 days after implantation.

2. The bioerodible implant of claim 1 wherein the corticosteroid is selected from the group consisting of cortisone, dexamethasone, fluocinolone, hydrocortisone, methylprednisolone, prednisolone, prednisone, triamcinolone, and any derivative thereof.

3. The bioerodible implant of claim 2 wherein the corticosteroid comprises dexamethasone.

4. The bioerodible implant of claim 1 wherein the corticosteroid is about 10 to about 90 percent by weight of the bioerodible implant.

5. The bioerodible implant of claim 4 wherein the corticosteroid is about 60 percent by weight of the bioerodible implant.

6. The bioerodible implant of claim 1 wherein the biodegradable polymer matrix comprises a polyester.

7. The bioerodible implant of claim 6 wherein the biodegradable polymer matrix comprises poly(lactic-co-glycolic) acid (PLGA) copolymer.

8. The bioerodible implant of claim 7 wherein the ratio of lactic to glycolic acid monomers is about 50/50 weight percentage.

* * * * *

UNITED STATES PATENT AND TRADEMARK OFFICE
CERTIFICATE OF CORRECTION

| | | |
|---|---|---|
| PATENT NO. | : 8,034,370 B2 | Page 1 of 1 |
| APPLICATION NO. | : 11/931954 | |
| DATED | : October 11, 2011 | |
| INVENTOR(S) | : Jane-Guo Shiah et al. | |

It is certified that error appears in the above-identified patent and that said Letters Patent is hereby corrected as shown below:

On the first page, in field (74), in "Attorney, Agent, or Firm", in column 2, line 1, delete "Wollenberge;" and insert -- Wollenberger; --, therefor.

On page 2, in column 2, under "Other Publications", line 5, delete "Substained" and insert -- Sustained --, therefor.

On page 3, in column 1, under "Other Publications", line 25, delete "Böake," and insert -- Böke, --, therefor.

On page 3, in column 1, under "Other Publications", line 36, delete "Aminopeptidease" and insert -- Aminopeptidase --, therefor.

On page 3, in column 2, under "Other Publications", line 33, delete "Schachat,," and insert -- Schachat, --, therefor.

On page 4, in column 1, under "Other Publications", line 24, delete "Polyactic" and insert -- Polylactic --, therefor.

On page 4, in column 1, under "Other Publications", line 24, delete "Biogradable" and insert -- Biodegradable --, therefor.

On page 4, in column 2, under "Other Publications", line 4, delete "Biogradable" and insert -- Biodegradable --, therefor.

On page 4, in column 2, under "Other Publications", line 10, delete "Acetysalicyclic" and insert -- Acetylsalicylic --, therefor.

On page 6, in column 2, under "Other Publications", line 11, delete "Introcular" and insert -- Intraocular --, therefor.

Signed and Sealed this
Twenty-second Day of May, 2012

David J. Kappos
*Director of the United States Patent and Trademark Office*